(12) United States Patent
Bondy et al.

(10) Patent No.: US 8,637,531 B2
(45) Date of Patent: *Jan. 28, 2014

(54) PYRIDO(3,2-D)PYRIDMIDINES USEFUL FOR TREATING VIRAL INFECTIONS

(75) Inventors: Steven S. Bondy, Danville, CA (US); William J. Watkins, Saratoga, CA (US); Lee S. Chong, Newark, CA (US); Piet Andre Maurits Maria Herdewijn, Rotselaar/Wexemaal (BE); Steven Cesar Alfons De Jonghe, Brugge (BE)

(73) Assignee: Gilead Sciences, Inc., Foster City, CA (US)

( * ) Notice: Subject to any disclaimer, the term of this patent is extended or adjusted under 35 U.S.C. 154(b) by 483 days.

This patent is subject to a terminal disclaimer.

(21) Appl. No.: 12/519,500

(22) PCT Filed: Dec. 24, 2007

(86) PCT No.: PCT/EP2007/011495
§ 371 (c)(1),
(2), (4) Date: Jun. 16, 2009

(87) PCT Pub. No.: WO2008/077650
PCT Pub. Date: Jul. 3, 2008

(65) Prior Publication Data
US 2010/0048559 A1    Feb. 25, 2010

Related U.S. Application Data

(60) Provisional application No. 60/871,916, filed on Dec. 26, 2006.

(51) Int. Cl.
| | | |
|---|---|---|
| *A01N 43/90* | (2006.01) | |
| *A61K 31/519* | (2006.01) | |
| *C07D 471/00* | (2006.01) | |
| *C07D 487/00* | (2006.01) | |

(52) U.S. Cl.
USPC .................. 514/264.1; 514/264.11; 544/279

(58) Field of Classification Search
USPC .................... 514/264.1; 544/264.11
See application file for complete search history.

(56) References Cited

U.S. PATENT DOCUMENTS

| | | |
|---|---|---|
| 2,924,599 A | 2/1960 | Oakes et al, |
| 3,939,268 A | 2/1976 | Nickl et al. |
| 4,460,591 A | 7/1984 | DeGraw et al. |
| 5,167,963 A | 12/1992 | DeGraw et al. |
| 5,508,281 A | 4/1996 | Gangjee |
| 5,521,190 A | 5/1996 | Henrie, II et al. |
| 5,654,307 A | 8/1997 | Bridges et al. |
| 6,476,031 B1 | 11/2002 | Chakravarty et al. |
| 6,713,484 B2 | 3/2004 | Bridges et al. |
| 6,723,726 B1 | 4/2004 | Cockerill et al. |
| 6,730,682 B2 | 5/2004 | Schnute et al. |
| 2002/0049207 A1 | 4/2002 | McCarthy |
| 2003/0186987 A1 | 10/2003 | Bridges et al. |
| 2003/0199526 A1 | 10/2003 | Choquette et al. |
| 2004/0039000 A1 | 2/2004 | Gangjee |
| 2004/0106616 A1 | 6/2004 | Bakthavatchalam et al. |
| 2008/0312227 A1* | 12/2008 | De Jonghe et al. ........ 514/234.2 |
| 2009/0131414 A1* | 5/2009 | De Jonghe et al. .......... 514/218 |
| 2009/0324543 A1* | 12/2009 | Watkins et al. ............. 424/85.4 |

FOREIGN PATENT DOCUMENTS

| | | | |
|---|---|---|---|
| WO | WO-01/83456 A1 | 11/2001 | |
| WO | WO-02/22602 A2 | 3/2002 | |
| WO | WO-02/22607 A1 | 3/2002 | |
| WO | WO-03/062209 A2 | 7/2003 | |
| WO | WO-2006/069805 A2 | 7/2006 | |
| WO | WO 2006/135993 | * 12/2006 | .......... C07D 471/04 |
| WO | WO-2006/135993 A1 | 12/2006 | |

OTHER PUBLICATIONS

Baba et al. (1984) "Synergistic Antiviral Effects of Antiherpes Compounds and Human Leukocyte Interferon on Varicella-Zoster Virus In Vitro," *Antimicrobial Agents and Chemotherapy* 25(4):515-517.
Elion et al. (1954) "Antagonists of Nucleic Acid Derivatives," *J. Biol Chem.* 208:477-488.
International Search Report and Written Opinion from PCT/USEP2007/011495, International Filing Date Dec. 24, 2007.

* cited by examiner

*Primary Examiner* — Erich A Leeser

(57) ABSTRACT

This invention provides pyrido(3,2-d)pyrimidine derivatives represented by the structural formula (I), wherein: $R_1$ is amino, $R_4$ is hydrogen, and $R_2$ and $R_3$ together provide a specific substitution pattern, pharmaceutical acceptable addition salts, stereochemical isomeric forms, N-oxides, solvates and pro-drugs thereof, are useful in the treatment of hepatitis C.

19 Claims, 2 Drawing Sheets

PYRIDO(3,2-D)PYRIDMIDINES USEFUL FOR TREATING VIRAL INFECTIONS

This is a U.S. national stage application, filed under 35 U.S.C. 371, of PCT/EP2007/011495, filed Dec. 24, 2007, claiming priority to U.S. Provisional Application Ser. No. 60/871,916, filed Dec. 26, 2006. The content of the provisional application is herein incorporated by reference in its entirety for all purposes.

The present invention relates to a class of novel trisubstituted pyrido(3,2-d)pyrimidine derivatives. This invention also relates to pharmaceutical compositions comprising said trisubstituted pyrido(3,2-d)pyrimidine derivatives and one or more pharmaceutically acceptable excipients. The present invention further relates to the use of said trisubstituted pyrido (3,2-d)pyrimidine derivatives as biologically active ingredients for manufacturing medicaments for the prevention or treatment of infection by a virus of the Flaviridae family, more specifically for inhibiting replication of hepatitis C virus.

BACKGROUND OF THE INVENTION

A huge number of pyrido(3,2-d)pyrimidine derivatives is already known in the art. For instance pyrido(3,2-d)pyrimidine derivatives with various substituents on positions 2, 4 and 6 (using the standard atom numbering for the pyrido(3, 2-d)pyrimidine moiety) are known with biological activities such as competitive inhibition of pteroylglutamic acid, inhibition of thrombocyte aggregation and adhesiveness, antineoplastic activity, inhibition of dihydrofolate reductase and thymidylate synthase, e.g. from U.S. Pat. No. 2,924,599, U.S. Pat. No. 3,939,268, U.S. Pat. No. 4,460,591, U.S. Pat. No. 5,167,963 and U.S. Pat. No. 5,508,281.

Pyrido(3,2-d)pyrimidine derivatives with various substituents on positions 2, 4, 6 and 7 (using the standard atom numbering for the pyrido(3,2-d)pyrimidine moiety), some of them with biological activities, are also known e.g. from U.S. Pat. No. 5,521,190, U.S. patent application publication No. 2002/0049207, U.S. patent application publication No. 2003/0186987, U.S. patent application publication No. 2003/0199526, U.S. patent application publication No. 2004/0039000, U.S. patent application publication No. 2004/0106616, U.S. Pat. No. 6,713,484, U.S. Pat. No. 6,730,682 and U.S. Pat. No. 6,723,726.

U.S. Pat. No. 5,654,307 discloses pyrido(3,2-d)pyrimidine derivatives substituted on position 4 with monoarylamino or monobenzylamino, and on positions 6 and 7 with substituents each independently selected from the group consisting of lower alkyl, amino, lower alkoxy, mono- or dialkylamino, halogen and hydroxy. WO 01/083456 discloses pyrido(3,2-d)pyrimidine derivatives substituted on position 4 with morpholinyl and on position 2 with hydroxyphenyl or morpholinoethoxyphenyl, having PI3K and cancer inhibiting activity. U.S. Pat. No. 6,476,031 discloses substituted quinazoline derivatives, including (in reaction scheme 5) a series of pyrido (3,2-d)pyrimidine derivatives which are substituted on position 4 with hydroxy, chloro or an aryl, heteroaryl (including pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl), cycloaliphatic or cycloheteroaliphatic group being optionally spaced from the pyrido(3,2-d)pyrimidine ring by a linker such as NH. WO 02/22602 and WO 02/22607 disclose pyrazole and triazole compounds, including 2-(1-trifluoromethylphenyl)-4-fluorobenzopyrazolyl-pyrido(3,2-d)pyrimidine and 2-(1-tri-fluoromethylphenyl)-4-methyltriazolyl-pyrido (3,2-d)pyrimidine being useful as protein kinase inhibitors. WO 03/062209 discloses pyrido(3,2-d)pyrimidine derivatives substituted on position 7 with aryl or heteroaryl and on position 4 with monoarylamino or monoheteroarylamino and which may further be substituted on positions 2 and/or 6, being useful as capsaicin receptor modulators. WO 2006/069805 discloses pyrido(3,2-d)pyrimidine derivatives substituted on position 6 with aryl or heteroaryl and on both positions 2 and 4 with monoalkylamino, monocycloalkylamino, monoarylamino or monoarylalkylamino, and which may further be substituted on position 7, being useful in the treatment of a disease mediated by phosphodiesterase-4 activity. WO 2006/135993 discloses 2,4,6-trisubstituted pyrido(3,2-d)pyrimidine derivatives 2,4,6-trisubstituted useful in the treatment of hepatitis C.

However there is a continuous need in the art for specific and highly therapeutically active compounds for preventing or treating infections due to Flaviridae and pathologic conditions associated therewith, especially hepatitis C. In particular, there is a need in the art to provide drugs which are active against hepatitis C in a minor dose in order to replace existing drugs having significant side effects and to decrease treatment costs.

Hepatitis is an inflammation of the liver that is most often caused by infection with one of three viruses known as hepatitis A, B or C. Hepatitis A virus (HAV) infection is the most common cause of acute hepatitis, and usually resolves spontaneously after several weeks of acute symptoms. Hepatitis B virus (HBV) and hepatitis C virus (HCV) are the most common viral causes of chronic hepatitis, usually defined as liver inflammation persisting for more than six months. HCV is the second most common cause of viral hepatitis in general and most common cause of chronic hepatitis. The World Health Organization estimates that worldwide 170 million people (3% of the world's population) are chronically infected with HCV. These chronic carriers are at risk of developing cirrhosis and/or liver cancer. In studies with a 10 to 20 year follow-up, cirrhosis developed in 20-30% of the patients, 1-5% of whom may develop liver cancer during the next ten years. The 15% to 45% of persons with acute hepatitis C who do recover are not subject to long-term complications and do not need treatment. Since HCV and pestiviruses belong to the same virus family and share many similarities (such as, but not limited to, organisation of the genome, analogous gene products and replication cycle), pestiviruses may be adopted as a model virus and surrogate for HCV. For example the Bovine Viral Diarrhea Virus (BVDV) is closely related to hepatitis C virus (HCV) and may be used as a surrogate virus in drug development for HCV infection.

HCV is a representative and highly significant member of the Flaviviridae family, a family of positive-strand RNA viruses. This family includes the following genera: Genus *Flavivirus* (type species Yellow fever virus; others include West Nile virus and Dengue Fever), Genus *Hepacivirus* (type species Hepatitis C virus), and Genus *Pestivirus* (type species Bovine viral diarrhea virus (BVDV); others include classical swine fever or hog cholera). Contrary to other families of positive strand RNA viruses such as human immunodeficiency virus (HIV), HCV seems incapable of integrating into the host's genome. The primary immune response to HCV is mounted by cytotoxic T lymphocytes. Unfortunately, this process fails to eradicate infection in most people; in fact, it may contribute to liver inflammation and, ultimately, tissue necrosis. The ability of HCV to escape immune surveillance is the subject of much speculation. One likely means of viral persistence relies on the presence of closely related but heterogeneous populations of viral genomes. Further studies of these quasi-species enable classification of several genotypes and subtypes, which have clinical implications.

The diagnosis of hepatitis C is rarely made during the acute phase of the disease because the majority of people infected experience no symptoms during this phase of the disease. Those who do experience acute phase symptoms are rarely ill enough to seek medical attention. The diagnosis of chronic phase hepatitis C is also challenging due to the absence or lack of specificity of symptoms until advanced liver disease develops, which may not occur until decades into the disease.

Hepatitis C testing begins with serological blood tests used to detect antibodies to HCV. Anti-HCV antibodies can be detected in about 80% of patients within 15 weeks after exposure, in more than 90% of patients within 5 months after exposure, and in more than 97% of patients by 6 months after exposure. Overall, HCV antibody tests have a strong positive predictive value for exposure to the hepatitis C virus, but may miss patients who have not yet developed antibodies (seroconversion), or have an insufficient level of antibodies to detect. Anti-HCV antibodies indicate exposure to the virus, but cannot determine if ongoing infection is present. All persons with positive anti-HCV antibody tests must undergo additional testing for the presence of the hepatitis C virus itself to determine whether current infection is present. The presence of HCV may be tested by using molecular nucleic acid testing methods such as, but not limited to, polymerase chain reaction (PCR), transcription mediated amplification (TMA), or branched DNA amplification. All HCV nucleic acid molecular tests have the capacity to detect not only whether the virus is present, but also to measure the amount of virus present in the blood (the HCV viral load). The HCV viral load is an important factor in determining the probability of response to interferon-base therapy, but does not indicate disease severity nor the likelihood of disease progression.

The goal of treatment is to prevent complications of HCV infection. This is principally achieved by eradication of infection. Accordingly, treatment responses are frequently characterized by the results of HCV RNA testing. Infection is considered eradicated when there is a sustained virologic response (SVR), defined as the absence of HCV RNA in serum by a sensitive test at the end of treatment and 6 months later. Persons who achieve an SVR almost always have a dramatic earlier reduction in the HCV RNA level, referred to as an early virologic response (EVR). Continued absence of detectable virus at termination of treatment is referred to as end of treatment response (ETR). A patient is considered relapsed when HCV RNA becomes undetectable on treatment but is detected again after discontinuation of treatment. Persons in whom HCV RNA levels remain stable on treatment are considered as non-responders, while those whose HCV RNA levels decline but remain detectable are referred to as partial responders.

Current standard of care for HCV treatment is a combination of (pegylated) interferon alpha and the antiviral drug ribavirin for a period of 24 or 48 weeks, depending upon the viral genotype. Should treatment with pegylated ribavirin-interferon not return a viral load reduction after 12 weeks, the chance of treatment success is less than 1%. Current indication for treatment includes patients with proven hepatitis C virus infection and persistent abnormal liver function tests. SVR of 75% or better occur in people with genotypes HCV 2 and 3 within 24 weeks of treatment, about 50% in those with genotype 1 within 48 weeks of treatment and 65% for those with genotype 4 within 48 weeks of treatment. About 80% of hepatitis C patients in the United States exhibit genotype 1, whereas genotype 4 is more common in the Middle East and Africa.

Best results have been achieved with the combination of weekly subcutaneous injections of long-acting peginterferon alpha and oral ribavirin daily. Interferons are substances naturally released by cells in the body after viral invasion. Interferon alfa-2b and peginterferon alfa-2b are synthetic versions of these substances. The protein product is manufactured by recombinant DNA-technology. Second generation interferons are further derivatized by binding to inert polyethylene glycol, thereby altering the pharmacokinetic properties. Ribavirin is a nucleoside analogue, which disrupts viral replication of hepatitis C virus (HCV).

The most common side effects of HCV treatment with (pegylated) interferon include: a decrease in white blood cells and platelets, anemia, nausea, diarrhea, fever, chills, muscle and joint pain, difficulty in concentrating, thyroid dysfunction, hair loss, sleeplessness, irritability, mild to serious depression, and rarely, suicidal thoughts. Other serious adverse events include bone marrow toxicity, cardiovascular disorders, hypersensitivity, endocrine disorders, pulmonary disorders, colitis, pancreatitis, and ophthalmologic disorders (eye and vision problems). (Pegylated) interferon may also cause or make worse fatal or life-threatening neuropsychiatric, autoimmune, ischemic, and infectious disorders. Patients with persistently severe or worsening signs or symptoms of these conditions are advised to stop therapy.

The most common side effect of HCV treatment with ribavirin is anaemia, which can be treated with erythropoietin. Other side effects include mood swings, irritability, anxiety, insomnia, abdominal pain, nervousness, breathlessness, rash, hair loss, dry skin, nausea, diarrhoea, loss of appetite, dizziness and weight loss. Ribavirin can also cause birth defects. Ribavirin should not be taken in combination with certain HIV drugs such as, but not limited to, didanosine, since lactic acidosis with fatal hepatic steatosis (fatty liver) may occur. Special attention should be taken for treatment with HIV co-infection.

Although the liver is the primary target of infection, studies to better define the steps of HCV infection are greatly hampered by the lack of a suitable animal model for such studies. The recent development of sub-genomic HCV RNA replicons capable of autonomous replication in the human hepatoma cell line, Huh-7, has been a significant advance in the study of HCV biology. The sub-genomic HCV RNA replicon system provides a cell-based assay to evaluate inhibitors of HCV enzymes like the protease, helicase, and RNA-dependant RNA polymerase or to evaluate nucleic acid targeting strategies like antisense RNA and ribozymes.

Targets for HCV Drug development include HCV-encoded enzymes, namely, NS2-3 and NS3-4A proteases, NS3 helicase, and NS5B RNA dependant RNA polymerase. Alternatively, HCV replication can be inhibited by blocking other HCV-encoded proteins such as NS5A or by the conserved RNA elements employing a nucleic acid based approach including antisense oligonucleotides, ribozymes, RNA aptamers, RNA decoys, and RNA interference. A major drawback for such nucleic acid based approaches is the size and charge of the nucleic acids, and their usually low physiological stability that do not allow for oral administration. Another target option for therapy is by blocking viral entry into the cell by obstruction of binding to HCV receptors such as, but not limited to, CD 209L and L-SIGN.

There is a strong need in the art to improve, or to provide alternatives to, the existing prophylactic or therapeutic solutions to infections by a virus of the Flaviridae family, more specifically HCV infection. In particular there is still a need in the art for providing alternative synthetic molecules having significant HCV replication inhibiting activity. There is also a need in the art for providing effective inhibiting molecules which are free from the significant drawbacks of the current drugs like pegylated interferon and ribavirin. Meeting these various needs in the art constitutes the main goal of the present invention.

SUMMARY OF THE INVENTION

The present invention is based on the unexpected finding that certain specific combinations of substituents on positions 2, 4 and 6 of the pyrido(3,2-d)pyrimidine core structure (using the atom numbering resulting from standard nomenclature) which are not suggested by the available prior art are however able to meet one or more of the needs recited herein above, in particular to achieve derivatives having desirable pharmacological properties such as an improved or specific activity against infection by a virus of the Flaviridae family, more particularly a significant or improved HCV replication inhibiting activity.

Based on this finding the present invention relates, in a first embodiment, to a class of trisubstituted pyrido(3,2-d)pyrimidine derivatives represented by the structural formula (I):

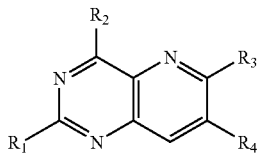

wherein:
  $R_1$ is amino;
  $R_2$ is selected from the group consisting of $C_{1-6}$ alkyl thio-$C_{1-6}$ alkoxy, $C_{2-6}$ alkenyloxy, $C_{2-6}$ alkynyloxy, $C_{3-10}$ cycloalkenyloxy, $C_{3-10}$ cycloalkenyl-$C_{1-6}$ alkoxy, $C_{1-6}$ alkylsulfonyl $C_{1-6}$ alkoxy, arylsulfonyl $C_{1-6}$ alkoxy, 2-propoxyethoxy, 2-butoxyethoxy, 2-ethoxy-1-propoxy, 2-isopropoxyethoxy, 2,2-difluoroethoxy, cyclobutoxy, cyclopentylmethoxy, cyclopropylmethoxy, 1-cyclopropylethoxy, 2-cyclopropylethoxy, cyclopentoxy, 3-methyl-3-methoxy-butoxy, tetrahydrofuranoxy, hexahydrofurofuranoxy, 1-ethylpropoxy, morpholinylethoxy, morpholinylpropoxy, morpholinylbutoxy, 2-methoxy-ethoxy, cyclohexyloxy, tetrahydropyranoxy, tetrahydropyranmethoxy, tetrahydrofuranmethoxy, 1-methoxy-2-propoxy, oxetan-3-yloxy and 2-ethoxyethoxy;
  $R_4$ is hydrogen;
  $R_3$ is selected from the group consisting of halogen, heterocyclic and aryl groups, wherein said heterocyclic or aryl groups are optionally substituted with one or more substituents independently selected from the group consisting of amino, amino-$C_{1-4}$ alkyl, acyl, di-$C_{1-4}$ alkylaminocarbonyl, $C_{1-4}$ alkoxy, $C_{1-4}$ alkylthio, $C_{1-4}$ alkyl, carboxylic acid (carboxy), hydroxy, halogen, halo-$C_{1-4}$ alkyl, hydroxy-$C_{1-4}$ alkyl, halo-$C_{1-4}$ alkoxy, $C_{2-8}$ alkenyl, $C_{1-2}$ alkylenedioxy, $C_{1-4}$ alkylsulfonyl, $C_{1-4}$ alkoxycarbonyl, $C_{1-4}$ alkylcarbonyl-amino di-$C_{1-4}$ alkylamino, di-$C_{1-4}$ alkylamino-$C_{1-4}$ alkyl, aryl, aryl-$C_{1-4}$ alkoxy, aryloxy, formyl, heterocyclic, heterocyclic-oxy, tri-$C_{1-4}$ alkylammonium-$C_{1-4}$alkyl, $C_{1-4}$ alkylcarbonyl, $C_{1-4}$ alkylcarbonylamino, arylsulfonyl and heterocyclic-substituted $C_{1-4}$alkyl;
or a pharmaceutical acceptable addition salt thereof or a stereochemical isomeric form thereof or a N-oxide thereof or a solvate thereof or a pro-drug thereof.

Within this first embodiment, the present invention relates to a sub-group of tri-substituted pyrido(3,2-d)pyrimidines represented by the structural formula (I), in particular wherein $R_3$ is halogen, which are useful as intermediates for making biologically-active pyrido(3,2-d)pyrimidine derivatives.

In a second embodiment, the present invention relates to the unexpected finding that desirable pharmacological properties such as an antiviral activity, especially against infection by a virus of the Flaviridae family, more specifically the ability to inhibit hepatitis C virus (HCV) replication, is present in a sub-group of compounds having the structural formula (I) with the proviso that $R_3$ is not halogen, as well as in other individual species of tri-substituted pyrido(3,2-d) pyrimidines.

As a consequence, the invention relates to the manufacture of pharmaceutical compositions comprising one or more pharmaceutically acceptable carriers and, as a biologically active principle, a therapeutically effective amount of at least one tri-substituted pyrido(3,2-d)pyrimidine derivative represented by the structural formula (I), with the proviso that $R_3$ is not halogen, as well as in other individual species of tri-substituted pyrido(3,2-d)pyrimidines, and/or a pharmaceutically acceptable addition salt thereof and/or a stereochemical isomeric form thereof and/or a N-oxide thereof and/or a solvate thereof and/or a pro-drug thereof.

As a result of their biological properties mentioned hereinabove, compounds represented by the structural formula (I), with the proviso that $R_3$ is not halogen, as well as in other individual species of tri-substituted pyrido(3,2-d)pyrimidines, are highly active anti-flaviridae agents, especially anti-HCV agents which, together with one or more pharmaceutically acceptable carriers, may be formulated into pharmaceutical compositions for the prevention or treatment of pathologic conditions such as, but not limited to, hepatitis C infection. It has furthermore been surprisingly found that their activity is virus-specific.

In a further embodiment, the present invention relates to combined preparations containing at least one compound represented by the structural formula (I), with the proviso that $R_3$ is not halogen, as well as in other individual species of tri-substituted pyrido(3,2-d)pyrimidines, and one or more antiviral agents, especially one or more other anti-flaviridae agents. In a further embodiment, the present invention relates to the prevention or treatment of the above-cited pathologic conditions or infections by administering to the patient in need thereof a therapeutically effective amount of a compound represented by the structural formula (I), with the proviso that $R_3$ is not halogen, as well as in other individual species of tri-substituted pyrido(3,2-d)pyrimidines, optionally in the form of a pharmaceutical composition or a combined preparation with one or more other suitable drugs, in particular antiviral agents.

In another embodiment, the present invention relates to various processes and methods for making the novel pyrido (3,2-d)pyrimidine derivatives defined by the structural formula (I), as well as in other individual species of tri-substituted pyrido(3,2-d)pyrimidines, including their pharmaceutically acceptable salts, N-oxides, solvates, pro-drugs and/or stereochemical isomeric forms, e.g. via one or more groups of tri-substituted pyrido(3,2-d)pyrimidine intermediates.

DEFINITIONS

Figure 1:
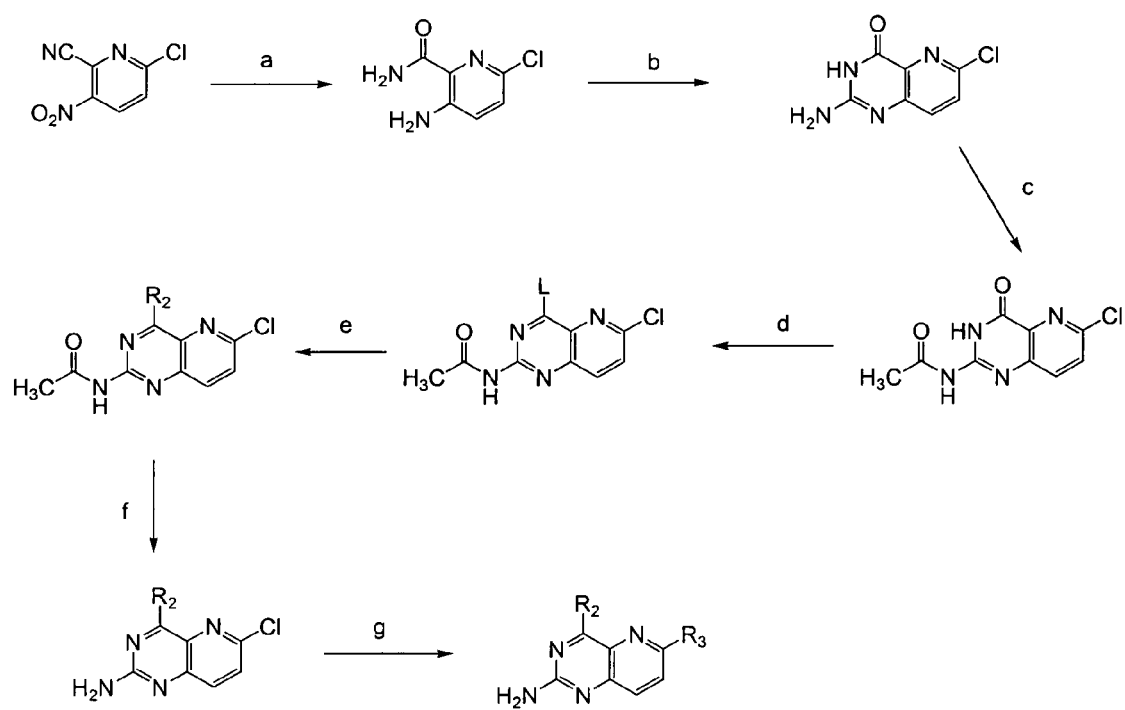
FIG. 1 schematically shows a first method for making 2,4,6-tri-substituted pyrido(3,2-d)pyrimidine derivatives represented by the formula (I) wherein the substituent in position 2 is amino, as well as intermediates therefor wherein the substituent in position 2 is a N-protected amino such as acylamino and/or wherein the substituent in position 4 is hydroxy, chloro or triazolyl.

Unless otherwise stated herein, the term "tri-substituted" means that three of the carbon atoms being in positions 2, 4 and 6 of the pyrido(3,2-d)pyrimidine core structure (according to standard atom numbering for the pyrido(3,2-d)pyrimidine moiety) are substituted with an atom or group of atoms other than hydrogen.

As used herein with respect to a substituting radical, and unless otherwise stated, the term "$C_{1-6}$ alkyl" means straight and branched chain saturated acyclic hydrocarbon monovalent radicals having from 1 to 6 carbon atoms such as, for example, methyl, ethyl, propyl, n-butyl, 1-methylethyl (isopropyl), 2-methylpropyl (isobutyl), 1,1-dimethylethyl (tert-butyl), 2-methylbutyl, n-pentyl, dimethylpropyl, n-hexyl, 2-methylpentyl, 3-methylpentyl, and the like. By analogy, the term "$C_{1-4}$ alkyl" refers to such radicals having from 1 to 4 carbon atoms.

As used herein with respect to a substituting radical, and unless otherwise stated, the terms "$C_{2-8}$ alkenyl" designate a straight and branched acyclic hydrocarbon monovalent radical having one or more ethylenic unsaturations and having from 2 to 8 carbon atoms such as, for example, vinyl, 1-propenyl, 2-propenyl (allyl), 1-butenyl, 2-butenyl, 2-pentenyl, 3-pentenyl, 3-methyl-2-butenyl, 3-hexenyl, 2-hexenyl, 2-heptenyl, 1,3-butadienyl, pentadienyl, hexadienyl, heptadienyl, heptatrienyl, octenyl and the like, including all possible isomers thereof.

As used herein with respect to a substituting radical, and unless otherwise stated, the term "$C_{3-10}$ cycloalkenyl" means a monocyclic mono- or polyunsaturated hydrocarbon monovalent radical having from 3 to 8 carbon atoms, such as for instance cyclopropenyl, cyclobutenyl, cyclopentenyl, cyclopentadienyl, cyclohexenyl, cyclohexadienyl, cycloheptenyl, cyclohepta-dienyl, cycloheptatrienyl, cyclooctenyl, cyclooctadienyl and the like, or a $C_{7-10}$ polycyclic mono- or polyunsaturated hydrocarbon mono-valent radical having from 7 to 10 carbon atoms such as dicyclopentadienyl, fenchenyl (including all isomers thereof, such as α-pinolenyl), bicyclo[2.2.1]hept-2-enyl, bicyclo[2.2.1]hepta-2,5-dienyl, cyclo-fenchenyl and the like.

As used herein with respect to a substituting radical, and unless otherwise stated, the term "$C_{2-6}$ alkynyl" defines straight and branched chain hydrocarbon radicals containing one or more triple bonds and optionally at least one double bond and having from 2 to 6 carbon atoms such as, for example, acetylenyl, 1-propynyl, 2-propynyl, 1-butynyl, 2-butynyl, 2-pentynyl, 1-pentynyl, 3-methyl-2-butynyl, 3-hexynyl, 2-hexynyl, 1-penten-4-ynyl, 3-penten-1-ynyl, 1,3-hexadien-1-ynyl and the like.

As used herein with respect to a substituting radical, and unless otherwise stated, the term "acyl" broadly refers to a substituent derived from an acid such as an organic monocarboxylic acid, a carbonic acid, a carbamic acid (resulting into a carbamoyl substituent) or the thioacid or imidic acid (resulting into a carbamidoyl substituent) corresponding to said acids, and the term "sulfonyl" refers to a substituent derived from an organic sulfonic acid, wherein said acids comprise an aliphatic, aromatic or heterocyclic group in the molecule. A more specific, but not limiting, kind of "acyl" group within the scope of the above definition refers to a carbonyl(oxo) group adjacent to a $C_{1-7}$ alkyl, a $C_{3-10}$ cycloalkyl, an aryl, an arylalkyl or a heterocyclic group, all of them being such as herein defined. Suitable examples of acyl groups are to be found below.

Acyl and sulfonyl groups originating from aliphatic or cycloaliphatic monocarboxylic acids are designated herein as aliphatic or cycloaliphatic acyl and sulfonyl groups and include, but are not limited to, the following:

alkanoyl (for example formyl, acetyl, propionyl, butyryl, isobutyryl, valeryl, isovaleryl, pivaloyl and the like);
  cycloalkanoyl (for example cyclobutanecarbonyl, cyclopentanecarbonyl, cyclohexanecarbonyl, 1-adamantanecarbonyl and the like);
  cycloalkyl-alkanoyl (for example cyclohexylacetyl, cyclopentylacetyl and the like);
  alkenoyl (for example acryloyl, methacryloyl, crotonoyl and the like);
  alkylthioalkanoyl (for example methylthioacetyl, ethylthioacetyl and the like);
  alkanesulfonyl (for example mesyl, ethanesulfonyl, propanesulfonyl and the like);
  alkoxycarbonyl (for example methoxycarbonyl, ethoxycarbonyl, propoxycarbonyl, isopropoxycarbonyl, butoxycarbonyl, isobutoxycarbonyl and the like);
  alkylcarbamoyl (for example methylcarbamoyl and the like);
  (N-alkyl)-thiocarbamoyl (for example (N-methyl)-thiocarbamoyl and the like);
  alkylcarbamidoyl (for example methylcarbamidoyl and the like); and
  alkoxyalkyl (for example methoxyalkyl, ethoxyalkyl, propoxyalkyl and the like);

Acyl and sulfonyl groups may also originate from aromatic monocarboxylic acids and include, but are not limited to, the following:

aroyl (for example benzoyl, toluoyl, xyloyl, 1-naphthoyl, 2-naphthoyl and the like);
  arylalkanoyl (for example phenylacetyl and the like);
  arylalkenoyl (for example cinnamoyl and the like);
  aryloxyalkanoyl (for example phenoxyacetyl and the like);
  arylthioalkanoyl (for example phenylthioacetyl and the like);
  arylaminoalkanoyl (for example N-phenylglycyl, and the like);
  arylsulfonyl (for example benzenesulfonyl, toluenesulfonyl, naphthalene sulfonyl and the like);
  aryloxycarbonyl (for example phenoxycarbonyl, naphthyloxycarbonyl and the like);
  arylalkoxycarbonyl (for example benzyloxycarbonyl and the like);
  arylcarbamoyl (for example phenylcarbamoyl, naphthylcarbamoyl and the like);
  arylglyoxyloyl (for example phenylglyoxyloyl and the like).
  arylthiocarbamoyl (for example phenylthiocarbamoyl and the like); and
  arylcarbamidoyl (for example phenylcarbamidoyl and the like).

Acyl groups may also originate from an heterocyclic monocarboxylic acids and include, but are not limited to, the following:

heterocyclic-carbonyl, in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiophenoyl, furoyl, pyrrolecarbonyl, nicotinoyl and the like); and heterocyclic-alkanoyl in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiopheneacetyl, furylacetyl, imidazolylpropionyl, tetrazolylacetyl, 2-(2-amino-4-thiazolyl)-2-methoxyiminoacetyl and the like).

As used herein with respect to a substituting radical, and unless otherwise stated, the term "$C_{3-10}$ cycloalkyl" refers to a mono- or polycyclic saturated hydrocarbon monovalent radical having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

As used herein with respect to a substituting radical, and unless otherwise stated, the term "aryl" designates any mono- or polycyclic aromatic monovalent hydrocarbon radical having from 6 up to 30 carbon atoms such as but not limited to phenyl, naphthyl, anthracenyl, phenanthracyl, fluoranthenyl, chrysenyl, pyrenyl, biphenyl, terphenyl, picenyl, indenyl, biphenyl, indacenyl, benzocyclobutenyl, benzocyclooctenyl and the like, including fused benzo-$C_{4-8}$ cycloalkyl radicals (the latter being as defined above) such as, for instance, indanyl, tetrahydronaphthyl, fluorenyl and the like, all of the said radicals being optionally substituted with one or more substituents independently selected from the group consisting of halogen, amino, trifluoromethyl, hydroxyl, sulfhydryl and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein with respect to a substituting radical, and unless otherwise stated, the terms "heterocyclic" or "heterocyclyl" refer to a mono- or polycyclic, saturated or mono-unsaturated or polyunsaturated monovalent hydrocarbon radical having from 2 up to 15 carbon atoms and including one or more heteroatoms in one or more heterocyclic rings, each of said rings having from 3 to 10 atoms (and optionally further including one or more heteroatoms attached to one or more carbon atoms of said ring, for instance in the form of a carbonyl or thiocarbonyl or selenocarbonyl group, and/or to one or more heteroatoms of said ring, for instance in the form of a sulfone, sulfoxide, N-oxide, phosphate, phosphonate or selenium oxide group), each of said heteroatoms being independently selected from the group consisting of nitrogen, oxygen, sulfur, selenium and phosphorus, also including radicals wherein a heterocyclic ring is fused to one or more aromatic hydrocarbon rings for instance in the form of benzo-fused, dibenzo-fused and naphtho-fused heterocyclic radicals; within this definition are included heterocyclic radicals such as, but not limited to, diazepinyl, oxadiazinyl, thiadiazinyl, dithiazinyl, triazolonyl, diazepinonyl, triazepinyl, triazepinonyl, tetrazepinonyl, benzoquinolinyl, benzothiazinyl, benzothiazinonyl, benzoxa-thiinyl, benzodioxinyl, benzodithiinyl, benzoxazepinyl, benzothiazepinyl, benzodiazepinyl, benzodioxepinyl, benzodithiepinyl, benzoazocinyl, benzo-thiazocinyl, benzodiazocinyl, benzoxathiocinyl, benzodioxocinyl, benzotrioxepinyl, benzoxathiazepinyl, benzoxadiazepinyl, benzothia-diazepinyl, benzotriazepinyl, benzoxathiepinyl, benzotriazinonyl, benzoxazolinonyl, azetidinonyl, azaspiroundecyl, dithiaspirodecyl, selenazinyl, selenazolyl, selenophenyl, hypoxanthinyl, azahypo-xanthinyl, bipyrazinyl, bipyridinyl, oxazolidinyl, diselenopyrimidinyl, benzodioxocinyl, benzopyrenyl, benzopyranonyl, benzophenazinyl, benzoquinolizinyl, dibenzo-carbazolyl, dibenzoacridinyl, dibenzophenazinyl, dibenzothiepinyl, dibenzoxepinyl, dibenzopyranonyl, dibenzoquinoxalinyl, dibenzothiazepinyl, dibenzisoquinolinyl, tetraazaadamantyl, thiatetraazaadamantyl, oxauracil, oxazinyl, dibenzothiophenyl, dibenzofuranyl, oxazolinyl, oxazolonyl, azaindolyl, azolonyl, thiazolinyl, thiazolonyl, thiazolidinyl, thiazanyl, pyrimidonyl, thiopyrimidonyl, thiamorpholinyl, aziactonyl, naphthindazolyl, naphthindolyl, naphthothiazolyl, naphthothioxolyl, naphthoxindolyl, naphthotriazolyl, naphthopyranyl, oxabicycloheptyl, azabenzimidazolyl, azacycloheptyl, azacyclooctyl, azacyclononyl, azabicyclononyl, tetrahydrofuryl, tetrahydropyranyl, tetrahydropyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl (benzothiofuranyl), phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, benzofuryl, quinolyl, quinazolinyl, quinoxalinyl, carbazolyl, phenoxazinyl, phenothiazinyl, xanthenyl, purinyl, benzothienyl, naphtothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimidazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, oxetanonyl, homopiperazinyl, homopiperidinyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzocarbazolyl, benzochromonyl, benzisoalloxazinyl, benzocoumarinyl, thiocoumarinyl, phenometoxazinyl, phenoparoxazinyl, phentriazinyl, thiodiazinyl, thiodiazolyl, indoxyl, thioindoxyl, benzodiazinyl (e.g. phthalazinyl), phthalidyl, phthalimidinyl, phthalazonyl, alloxazinyl, dibenzopyronyl (i.e. xanthonyl), xanthionyl, isatyl, isopyrazolyl, isopyrazolonyl, urazolyl, urazinyl, uretinyl, uretidinyl, succinyl, succinimido, benzylsultimyl, benzylsultamyl and the like, including all possible isomeric forms thereof, wherein each carbon atom of said heterocyclic ring may furthermore be independently substituted with a substituent selected from the group consisting of halogen, nitro, $C_{1-6}$ alkyl (optionally containing one or more functions or radicals selected from the group consisting of oxo, hydroxyl, ether, amino, cyano, nitro, formyl and hydroxylamino;

depending upon the number of unsaturations in the 3 to 10 atoms ring, heterocyclic radicals are conventionally sub-divided into heteroaromatic (or "heteroaryl") radicals and non-aromatic heterocyclic radicals; when a heteroatom of said non-aromatic heterocyclic radical is nitrogen, the latter may be substituted with a substituent selected from the group consisting of $C_{1-6}$ alkyl, $C_{3-10}$ cycloalkyl and aryl.

As used herein with respect to a substituting radical, and unless otherwise stated, the term "$C_{1-6}$ alkylthio" refers to a substituent wherein a carbon atom of a $C_{1-6}$ alkyl radical, is attached to a sulfur atom through a single bond such as, but not limited to, methylthio, ethylthio, isopropylthio and the like.

As used herein with respect to a substituting radical, and unless otherwise stated, the terms "$C_{1-6}$ alkoxy", "$C_{2-8}$ alkenyloxy", "$C_{2-6}$ alkynyloxy", "$C_{3-10}$ cycloalkenyl-$C_{1-6}$ alkoxy", "$C_{3-10}$ cycloalkenyloxy", "$C_{1-6}$ alkylthio-$C_{1-6}$ alkoxy", "heterocyclic-oxy", "heterocyclic-substituted $C_{1-6}$ alkoxy" and the like refer to substituents wherein a carbon atom of a $C_{1-6}$ alkyl, $C_{2-8}$ alkenyl, $C_{2-6}$ alkynyl, $C_{1-6}$ alkylthio-$C_{1-6}$ alkyl, $C_{3-10}$ cycloalkenyl, $C_{3-10}$ cycloalkenyl-$C_{1-6}$ alkyl, heterocyclic or heterocyclic-substituted $C_{1-6}$ alkyl radical (each of them such as defined herein), is attached to an oxygen atom through a single bond such as, but not limited to, methoxy, ethoxy, propoxy, butoxy, pentoxy, isopropoxy, sec-butoxy, tert-butoxy, pentoxy, methylbutenyloxy, pentynyloxy, methylsulfonylethoxy, methylthioethoxy, cyclohexenyloxy, cyclohexenylmethoxy, octenyloxy, heptadienyloxy, piperidinoxy, methylpiperidinoxy, pyrrolidinoxy, pyridinoxy, tetrahydrofuranyloxy, tetrahydropyranoxy, hexahydrofuranyloxy, tetrahydropyranylmethoxy, tetrahydrofuranylmethoxy, including all possible isomers thereof, and the like.

As used herein with respect to a substituting atom, and unless otherwise stated, the term halogen means any atom selected from the group consisting of fluorine, chlorine, bromine and iodine.

As used herein with respect to a substituting radical, and unless otherwise stated, the term "arylalkyl" refers to an aliphatic saturated hydrocarbon monovalent radical (preferably a $C_{1-6}$ alkyl radical such as defined above) onto which an aryl radical (such as defined above) is attached via a carbon atom, and wherein the said aliphatic radical and/or the said aryl radical may be optionally substituted with one or more substituents independently selected from the group consisting of halogen, amino, hydroxyl, trifluoromethyl and nitro, such as but not limited to benzyl, 4-chlorobenzyl, 4-fluorobenzyl, 2-fluorobenzyl, 3,4-dichlorobenzyl, 2,6-dichlorobenzyl, 3-methylbenzyl, 4-methylbenzyl, 4-ter-butylbenzyl, phenylpropyl, 1-naphthylmethyl, phenylethyl, 1-amino-2-phenylethyl, 1-amino-2-[4-hydroxy-phenyl]ethyl, and the like.

As used herein with respect to a substituting radical, and unless otherwise stated, the term "alkylamino" means that one (thus monosubstituted amino) or respectively two (thus disubstituted amino) $C_{1-6}$ alkyl radical(s) (as defined herein, respectively, is/are attached to a nitrogen atom through a single bond such as, but not limited to, methylamino, dimethylamino, ethylamino, diethylamino, isopropylamino, n-butylamino, tert-butylamino, dibutylamino.

As used herein and unless otherwise stated, the term "stereochemical isomeric form" refers to all possible different isomeric as well as conformational forms which the compounds represented by the structural formula (I) may possess, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a trisubstituted pyrido(3,2-d)pyrimidine derivative of this invention with a suitable inorganic solvent (e.g. hydrates) or organic solvent, such as but not limited to alcohols, ketones, esters, ethers, nitriles and the like.

DETAILED DESCRIPTION OF THE INVENTION

In a first embodiment of the present invention, the novel trisubstituted pyrido(3,2-d)pyrimidine derivatives are as defined in the structural formula (I), wherein each of the substituents $R_2$ and $R_3$ may independently correspond to any of the definitions given above, in particular with any of the individual species listed therein or with any particular meaning (such as illustrated above) of generic terms used for naming or designating substituting groups such as, but not limited to, "$C_{1-6}$ alkyl", "$C_{3-10}$ cycloalkyl", "aryl", "heterocyclic", "halogen", "arylalkyl", "$C_{1-6}$ alkoxy", "$C_{1-6}$ alkylthio" and the like.

Within the broad class of trisubstituted pyrido(3,2-d)pyrimidine derivatives represented by the structural formula (I), a useful sub-group of compounds is one wherein $R_3$ is a mono-substituted phenyl group and wherein the substituent of said phenyl group is located in para position with respect to the pyrido(3,2-d)pyrimidinyl core.

Within the broad class of trisubstituted pyrido(3,2-d)pyrimidine derivatives represented by the structural formula (I), another useful sub-group of compounds is one wherein $R_3$ is a mono-substituted phenyl group and wherein the substituent of said phenyl group is located in ortho position with respect to the pyrido(3,2-d)pyrimidinyl core.

Within the broad class of trisubstituted pyrido(3,2-d)pyrimidine derivatives represented by the structural formula (I), another useful sub-group of compounds is one wherein $R_3$ is a mono-substituted phenyl group and wherein the substituent of said phenyl group is located in meta position with respect to the pyrido(3,2-d)pyrimidinyl core.

Within the broad class of trisubstituted pyrido(3,2-d)pyrimidine derivatives represented by the structural formula (I), another useful sub-group of compounds is one wherein $R_3$ is a di-substituted phenyl group and wherein one substituent of said phenyl group is located in para position with respect to the pyrido(3,2-d)pyrimidinyl core.

Within the broad class of trisubstituted pyrido(3,2-d)pyrimidine derivatives represented by the structural formula (I), another useful sub-group of compounds is one wherein $R_3$ is a di-substituted phenyl group and wherein one substituent of said phenyl group is located in ortho position with respect to the pyrido(3,2-d)pyrimidinyl core.

Within the broad class of trisubstituted pyrido(3,2-d)pyrimidine derivatives represented by the structural formula (I), another useful sub-group of compounds is one wherein $R_3$ is a tri-substituted phenyl group such as, but not limited to, a sub-group wherein one substituent of said phenyl group is located in para position with respect to the pyrido(3,2-d)pyrimidinyl core and/or wherein at least two substituents are identical.

Within the broad class of trisubstituted pyrido(3,2-d)pyrimidine derivatives represented by the structural formula (I), another useful sub-group of compounds is one wherein $R_3$ is a phenyl group optionally substituted with one or more (e.g. two or three) substituents independently selected from the group consisting of amino, acetyl, acetamido, bromo, chloro, fluoro, aminomethyl, benzyloxy, phenyl, trifluoromethyl, methyl, carboxy, formyl, hydroxy, methoxy, ethoxy, trifluoromethoxy, cyano, dimethylamino, dimethylaminomethyl, methoxycarbonyl, ethoxycarbonyl, n-propoxycarbonyl, isopropoxycarbonyl, tert-butoxycarbonyl, hydroxymethyl, 3,4-methylenedioxy, methylthio, morpholinyl, nitro, phenoxy, tert-butoxycarbonylamino, tetrahydro-2H-pyran-2-yloxy, thien-2-yl and vinyl.

Within the broad class of trisubstituted pyrido(3,2-d)pyrimidine derivatives represented by the structural formula (I), another useful sub-group of compounds is one wherein $R_3$ is a naphthyl group optionally substituted with benzyloxy.

Within the broad class of trisubstituted pyrido(3,2-d)pyrimidine derivatives represented by the structural formula (I), another useful sub-group of compounds is one wherein $R_3$ is a heterocyclic group optionally substituted with one or more (e.g. two) substituents independently selected from the group consisting of acetamido, halogen (preferably bromo or chloro), methyl, isopropyl, methoxy, ethoxy, tert-butoxy, oxo, formyl, phenyl, methylsulfanyl, phenylsulfonyl and tert-butoxycarbonyl.

Within the broad class of trisubstituted pyrido(3,2-d)pyrimidine derivatives represented by the structural formula (I), another useful sub-group of compounds is one wherein $R_3$ is a heterocyclic group selected from the group consisting of 2-acetamidopyridin-5-yl, 2-benzothienyl, 1-benzothiophen-3-yl, 1-benzothiophen-2-yl, 2-bromo-3-chloropyridin-4-yl, 5-bromo-2,3-dihydrobenzo[b]furan-7-yl, 2-bromo-3-methylpyridin-5-yl, 2-bromopyridin-5-yl, 5-bromothien-2-yl, 2-chloro-6-isopropylpyridin-3-yl, 2-chloro-3-methylpyridin-5-yl, 5-chlorothien-2-yl, dibenzo[b,d]furan-4-yl, 2-chloro-3-fluoropyridin-4-yl, dibenzo[b,d]thien-4-yl, 3,4-dihydro-2H-1,5-benzodioxepin-7-yl, 2,5-dibromo-3-pyridinyl, 2,6-dichloro-pyridin-3-yl, 2,3-dihydro-1-benzofuran-5-yl, 2,4-dimethoxypyrimidin-5-yl, 3,5-dimethylisoxazol-4-yl, 1-[1,3]dioxolan-2-ylmethyl-4-1H-pyrazolyl, 2,4-dioxo-1,2, 34-tetrahydro-5-pyrimidinyl, 2,4-di(tert-butoxy)pyrimidin-5-yl, 2-ethoxypyridin-3-yl, 2-fluoro-3-methylpyridin-5-yl, 2-fluoropyridin-3-yl, 2-fluoropyridin-5-yl, 5-formyl-2-furyl, 5-formylthiophen-2-yl, furan-3-yl, furan-2-yl, 5-indolyl, isoquinolin-4-yl, 2-methoxypyrimidin-5-yl, 5-methyl-1-benzothiophen-2-yl, 5-methylfuran-2-yl, 5-methyl-3-phenyl-4-isoxazolyl, 5-(methylsulfanyl)-2-thienyl, 3-methyl-pyridin-2-yl, (5-methyl)thien-2-yl, 5-methylpyridin-2-yl, 5-methylpyridin-3-yl, 2-methoxypyridine-3-yl, (4-methyl)thien-2-yl, 2-methoxypyridin-5-yl, 1-(phenylsulfonyl)-1H-indol-3-yl, 1-(phenylsulfonyl)-1H-indol-3-yl, 5-phenyl-2-thienyl, pyridin-4-yl, pyridin-3-yl, 5-pyrimidinyl, 4-phenoxathiinyl, 8-quinolinyl, 3-quinolinyl, 1-tert-butoxycarbonyl-2-pyrrolyl, 1-(tert-butoxycarbonyl)-5-bromo-1H-indol-2-yl, 1-(tert-butoxycarbonyl)-1H-indol-2-yl, 1-(tert-butoxycarbonyl)-5-methoxy-1H-indol-2-yl, 1-thianthrenyl-3-thienyl and 2-thienyl.

The present invention further provides various processes and methods for making the novel trisubstituted pyrido(3,2-d)pyrimidine derivatives represented by the structural formula (I). As a general rule, the preparation of these compounds is based on the principle that, starting from a suitable pyrido(3,2-d)pyrimidine precursor (usually a 2,3,6-trisubstituted pyridine, method shown in FIG. 1) or from 2-amino-4-hydroxy-6-chloro-pyrido(3,2-d)pyrimidine (method shown in FIG. 2), each of the desirable substituents $R_2$ and $R_3$ may be introduced separately without adversely influencing, or being adversely influenced by, the amino substituent already present at position 2 on the pyrido(3,2-d)pyrimidine moiety or the capacity to introduce further substituents later on.

Methods of manufacture have been developed by the present inventors which may be used alternatively to, or may be combined with, the methods of synthesis already known in the art of pyrido(3,2-d)pyrimidine derivatives (depending upon the targeted final compound). For instance, the synthesis of mono- and di-N-oxides of the pyrido(3,2-d)pyrimidine derivatives of this invention can easily be achieved by treating the said derivatives with an oxidizing agent such as, but not limited to, hydrogen peroxide (e.g. in the presence of acetic acid) or a peracid such as chloroperbenzoic acid. The methods for making the pyrido(3,2-d)pyrimidine derivatives of the present invention will now be explained in more details by reference to the appended FIGS. 1 and 2 wherein, unless otherwise stated hereinafter, each of the substituting groups or atoms $R_2$, $R_3$, $R_4$ and $R_1$ is as defined in formula (I) of the summary of the invention and, more specifically, may correspond to any of the individual meanings disclosed above.

In the description of the reaction steps involved in each figure, reference is made to the use of certain catalysts and/or certain types of solvents. It should be understood that each catalyst mentioned should be used in a catalytic amount well known to the skilled person with respect to the type of reaction involved. Solvents that may be used in the following reaction steps include various kinds of organic solvents such as protic solvents, polar aprotic solvents and non-polar solvents as well as aqueous solvents which are inert under the relevant reaction conditions. More specific examples include aromatic hydrocarbons, chlorinated hydrocarbons, ethers, aliphatic hydrocarbons, alcohols, esters, ketones, amides, water or mixtures thereof, as well as supercritical solvents such as carbon dioxide (while performing the reaction under supercritical conditions). The suitable reaction temperature and pressure conditions applicable to each kind of reaction step will not be detailed herein but do not depart from the relevant conditions already known to the skilled person with respect to the type of reaction involved and the type of solvent used (in particular its boiling point).

FIG. 1 schematically shows a first method for making 2-amino-4,6-di-substituted pyrido(3,2-d)pyrimidine derivatives represented by the structural formula (I) through a series of intermediates. In step (a), the 3-nitro group of 6-chloro-2-cyano-3-nitropyridine is reduced, either catalytically (e.g. by using platinum or palladium under an atmosphere of hydrogen) or chemically (e.g. by using iron or tin under acidic conditions) and at the same time the 2-cyano group is hydrolyzed into a carboxamide function. A ring closure reaction leading to the formation of the pyrido[3,2-d]pyrimidine scaffold occurs in step (b) by treatment of 6-chloro-2-carboxamido-3-aminopyridine with a ring closure reagent such as, but not limited to, chloro-formamidine or guanidine. In step (c), the amino group at position 2 is protected, for example by means of an acyl group such as a pivaloyl group (not shown in FIG. 1) or acetyl group, by reaction with acetic anhydride or pivaloyl anhydride in pyridine as a solvent, thus resulting into the introduction of a N-protected amino group at position 2 such as, but not limited to, acetamido (shown in FIG. 1) or pivalamido. Activation of the tautomeric hydroxyl group at position 4 of the pyrido[3,2-d]pyrimidine scaffold for the subsequent nucleophilic displacement reaction occurs in step (d) by preparing the corresponding 4-(1,2,4-triazolyl)-pyrido[3,2-d]pyrimidine derivative or 4-chloro-pyrido[3,2-d]pyrimidine derivative. The 4-triazolyl derivative can be obtained by treating the 4-oxo-pyrido[3,2-d]pyrimidine derivative with $POCl_3$ or 4-chlorophenyl phosphorodichloridate and 1,2,4-triazole in an appropriate solvent such as, but not limited to, pyridine or acetonitrile. The 4-chloro derivative can be obtained by treating the 4-oxo-pyrido[3,2-d]pyrimidine derivative with thionyl chloride or $POCl_3$. The chlorine atom or triazolyl group is designated as L in FIG. 1. Nucleophilic displacement of the triazolyl group or chlorine atom occurs in step (e) by reaction with an appropriate nucleophile having the general formula $R_2H$, wherein $R_2$ is as defined in the general formula (I), in a polar aprotic solvent. Examples of suitable nucleophiles include, but are not limited to, sodium or potassium alkoxides that may, if desired, be formed in situ by any known method from the relevant alcohol. In step (f), the amino protecting group is cleaved off by using standard cleavage conditions such as acidic or basic hydrolysis. In the last step (g), the 2-amino-4-$R_2$-substituted-6-chloro-pyrido(3,2-d)pyrimidine derivative is subjected to a palladium-catalyzed reaction such as, but not limited to, a Suzuki reaction with a suitable aryl-boronic acid or heterocyclic boronic acid, or a pinacol ester thereof, i.e. wherein the aryl or heterocyclic group may include the relevant substituent(s), to yield the desired derivative.

Suitable aryl-boronic acids and pinacol esters thereof include, but are not limited to, the following commercially available materials wherein the aryl group is 3-acetamidophenyl, 4-acetamidophenyl, 4-acetylphenyl, 3-acetylphenyl, 2-acetylphenyl, 5-acetyl-2-chlorophenyl, 4-acetyl-3-fluorophenyl, 5-acetyl-2-fluorophenyl, 3-aminophenyl, 4-aminomethylphenyl, 3-aminophenyl, 4-benzyloxybenzene, 3-benzyloxybenzene, 2-benzyloxybenzene, 4-benzyloxy-2-fluorophenyl, 4-benzyloxy-3-fluorophenyl, biphenyl-3-, 3,5-bis(trifluoromethyl)-benzene, 4-bromophenyl, 3-bromophenyl, 4-bromo-2,5-dimethylphenyl, 2-bromo-5-fluorophenyl, 2-bromo-6-fluorophenyl, 4-carboxyphenyl, 2-carboxyphenyl, 2-carboxy-5-fluorophenyl, 4-carboxy-2-chlorophenyl, 5-carboxy-2-chlorophenyl, 4-carboxy-3-chlorophenyl, 3-carboxyphenyl, 2-chloro-5-formylphenyl, 2-chloro-5-hydroxyphenyl, 3-chloro-4-fluorophenyl, 2-chloro-4-fluorophenyl, 4-chloro-2-fluorophenyl, 3-chloro-5-methoxyphenyl, 2-chloro-4-methylphenyl, 2-chloro-5-methylphenyl, 2-chloro-5-trifluoromethoxyphenyl, 3-chloro-5-trifluoromethylphenyl, 4-chloro-2-trifluoromethyl-phenyl, 4-chlorophenyl, 3-chlorophenyl, 2-chlorophenyl, 4-cyanophenyl, 3-cyanophenyl, 2-cyanophenyl, 3,5-dibromophenyl, 2,6-dichlorophenyl, 3,4-dichlorophenyl, 2,4-dichlorophenyl, 2,3-dichlorophenyl, 3,5-dichlorophenyl, 3,5-difluorophenyl, 3,5-difluoro-2-methoxyphenyl, 3,4-difluorophenyl, 2,6-difluorophenyl, 2,5-difluorophenyl, 2,4-difluorophenyl, 2,3-difluorophenyl, 2,3-dihydro-1,4-benzodioxin-6-yl, 2,4-dimethoxybenzene, 4-(N,N-dimethylamino)phenyl, 2-(N,N-dimethylaminomethyl)phenyl, 3,5-dimethylphenyl, 3,4-dimethylphenyl, 2,6-dimethylphenyl, 2,6-dimethoxyphenyl, 2,5-dimethoxyphenyl, 2,4-dimethoxyphenyl, 4-ethoxyphenyl, 2-ethoxyphenyl, 4-ethoxycarbonylphenyl, 3-ethoxycarbonylphenyl, 2-ethoxycarbonylphenyl, 4-ethylphenyl, 4-fluorophenyl, 3-fluorophenyl, 2-fluorophenyl, 3-fluoro-4-formylphenyl, 4-fluoro-2-methylphenyl, 2-fluoro-5-methylphenyl, 4-fluoro-3-formylphenyl, 2-fluoro-5-methoxyphenyl, 5-fluoro-2-methoxycarbonylphenyl, 2-formyl-5-methoxyphenyl, 5-formyl-2-methoxyphenyl, 2-formyl-5-methylphenyl, 4-formylphenyl, 3-formylphenyl, 2-formylphenyl, 3-hydroxy-4-methoxycarbonylphenyl, 4-(hydroxymethyl)phenyl, 3-(hydroxymethyl)phenyl, 4-hydroxyphenyl, 3-hydroxyphenyl, 4-iodophenyl, 3-iodophenyl, 3-isopropoxycarbonyl-phenyl, 4-isopropoxycarbonylphenyl, 3-n-propoxycarbonylphenyl, 4-n-propoxycarbonylphenyl, 4-methanesulfonylphenyl, 2-methoxy-5-formylphenyl, 5-methoxy-2-formylphenyl, 4-methoxy-2-formylphenyl, 4-methoxycarbonylphenyl, 3-methoxycarbonylphenyl, 2-methoxycarbonylphenyl, 4-methoxyphenyl, 3-methoxyphenyl, 2-methoxyphenyl, 3,4-methylenedioxyphenyl, 4-methylphenyl, 2-methylphenyl, 4-(methylthio)phenyl, 3-(methylthio)phenyl, 4-morpholinophenyl, 3-morpholinophenyl, 4-nitrophenyl, 3-nitrophenyl, 2-nitrophenyl, 4-phenoxyphenyl, 2-phenoxyphenyl, 4-(tert-butoxycarbonylamino)-3-methoxyphenyl, 2-(tert-butoxycarbonyl)phenyl, 3-(tert-butoxycarbonyl)phenyl, 4-(tert-butoxycarbonyl)phenyl, 4-tert-butylphenyl, 4-(tetrahydro-2H-pyran-2-yloxy)phenyl, 4-(2-thienyl)phenyl, trans-α-styrene, 4-tolyl, 3-tolyl, 2-tolyl, 4-trifluoromethoxyphenyl, 4-(trimethylammonium)methylphenyl, 2,4,6-trimethylphenyl, 3,4,5-trifluorophenyl, 3-trifluoromethylphenyl, 4-trifluoromethoxyphenyl, 3-trifluoromethoxyphenyl, 3-trifluoromethylphenyl, 2-trifluoromethylphenyl, 3,4,5-trimethoxyphenyl, 4-vinylphenyl, 6-benzyloxy-2-naphthyl, 1-naphthyl, 2-naphthyl or 1-biphenylenyl.

Suitable heterocyclic-boronic acids and pinacol esters thereof include, but are not limited to, the following commercially available materials wherein the heterocyclic group is 2-acetamidopyridin-5-yl, 2-benzothienyl, 1-benzothiophen-3-yl, 1-benzothien-2-yl, 2-bromo-3-chloropyridin-4-yl, 5-bromo-2,3-dihydrobenzo[b]furan-7-yl, 2-bromo-3-methylpyridin-5-yl, 2-bromopyridin-5-yl, 5-bromothien-2-yl, 2-chloro-6-isopropylpyridin-3-yl, 2-chloro-3-methylpyridin-5-yl, 5-chlorothien-2-yl, dibenzo[b,d]-furan-4-yl, 2-chloro-3-fluoropyridin-4-yl, dibenzo[b,d]thien-4-yl, 3,4-dihydro-2H-1,5-benzodioxepin-7-yl, 2,5-dibromo-3-pyridinyl, 2,6-dichloro-pyridin-3-yl, 2,3-dihydro-1-benzofuran-5-yl, 2,4-dimethoxypyrimidin-5-yl, 3,5-dimethylisoxazol-4-yl, 1-[1,3]-dioxolan-2-ylmethyl-4-1H-pyrazolyl, 2,4-dioxo-1,2,34-tetrahydro-5-pyrimidinyl, 2,4-di(tert-butoxy)pyrimidin-5-yl, 2-ethoxypyridin-3-yl, 2-fluoro-3-methylpyridin-5-yl, 2-fluoropyridin-3-yl, 2-fluoropyridin-5-yl, 5-formyl-2-furyl, 5-formylthiophen-2-yl, furan-3-yl, furan-2-yl, 5-indolyl, isoquinolin-4-yl, 2-methoxypyrimidin-5-yl, 5-methyl-1-benzothiophen-2-yl, 5-methylfuran-2-yl, 5-methyl-3-phenyl-4-isoxazolyl, 5-(methylsulfanyl)-2-thienyl, 3-methyl-pyridin-2-yl, (5-methyl)thien-2-yl, 5-methylpyridin-2-yl, 5-methylpyridin-3-yl, 2-methoxypyridine-3-yl, (4-methyl)thien-2-yl, 2-methoxypyridin-5-yl, 1-(phenylsulfonyl)-1H-indol-3-yl, 1-(phenylsulfonyl)-1H-indol-3-yl, 5-phenyl-2-thienyl, pyridin-4-yl, pyridin-3-yl, 5-pyrimidinyl, 4-phenoxathiinyl, 8-quinolinyl, 3-quinolinyl, 1-tert-butoxycarbonyl-2-pyrrolyl, 1-(tert-butoxycarbonyl)-5-bromo-1H-indol-2-yl, 1-(tert-butoxycarbonyl)-1H-indol-2-yl, 1-(tert-butoxycarbonyl)-5-methoxy-1H-indol-2-yl, 1-thianthrenyl-3-thienyl or 2-thienyl.

Figure 2:
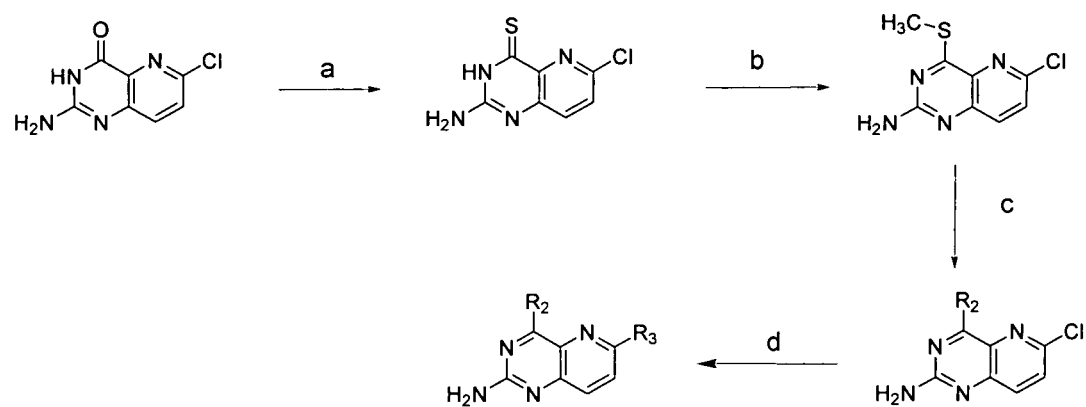
FIG. 2 schematically shows a second method for making 2,4,6-tri-substituted pyrido(3,2-d)pyrimidine derivatives represented by the formula (I) wherein the substituent in position 2 is amino, as well as intermediates therefor wherein the substituent in position 4 is sulfhydryl or methylthio.

FIG. 2 shows a second method for making 2-amino-4,6-di-substituted pyrido(3,2-d)pyrimidine derivatives, in particular as represented by the structural formula (I). In step (a), the tautomeric hydroxyl group at position 4 of the pyrido(3,2-d)pyrimidine scaffold is converted to the corresponding 4-sulfhydryl group by treatment with phosphorus pentasulfide or Lawesson's reagent. The method of step (a) can be performed whatever the type of substituent on position 6 and, although FIG. 2 shows a 6-chloro substituent, the method is not limited thereto and is also applicable when an optionally substituted aryl or heteroaryl group is present on position 6 of the pyrido(3,2-d)pyrimidine scaffold, as described for instance in WO 2006/069805. The resulting 2-amino-4- thioxo-6-substituted-pyrido(3,2-d)pyrimidine (6-chloro shown in FIG. 2) is then methylated in step (b) by treatment with iodomethane under alkaline conditions (e.g. using a 1 N NaOH solution). The thiomethyl group at position 4 is then displaced in step (c) by a nucleophile bearing the general formula $R_2H$, wherein $R_2$ is as defined in the general formula (I). Examples of suitable nucleophiles include, but are not limited to, sodium or potassium alkoxides that may, if desired, be formed in situ by any known method from the relevant alcohol. In step (d), the 2-amino-4-$R_2$-substituted-6-chloropyrido(3,2-d)pyrimidine derivative is subjected to a palladium-catalyzed reaction such as, but not limited to, a Suzuki reaction with a suitable aryl-boronic acid or heteroaryl-boronic acid, or a pinacol ester thereof, wherein the aryl or heteroaryl group may include one or more suitable substituent(s), to yield the desired trisubstituted pyrido(3,2-d)pyrimidine derivative, in particular one represented by the structural formula (I). Obviously step (d) is not required when an optionally substituted aryl or heteroaryl group is already present on position 6 of the pyrido(3,2-d)pyrimidine scaffold at the initial step of this method, as explained herein-above.

In another particular embodiment, the invention relates to a group of trisubstituted pyrido(3,2-d)pyrimidine derivatives, as well as pharmaceutical compositions comprising such trisubstituted pyrido(3,2-d)pyrimidine derivatives as active principle, and being in the form of a pharmaceutically acceptable salt. The latter include any therapeutically active non-toxic addition salt which compounds having the general formula (I), especially these wherein $R_3$ is not halogen, as well as other individual species of tri-substituted pyrido(3,2-d)pyrimidines are able to form with a salt-forming agent. Such addition salts may conveniently be obtained by treating the trisubstituted pyrido(3,2-d)pyrimidine derivatives of the invention with an appropriate salt-forming acid or base. For instance, trisubstituted pyrido(3,2-d)pyrimidine derivatives having basic properties may be converted into the corresponding therapeutically active, non-toxic acid addition salt form by treating the free base form with a suitable amount of an appropriate acid following conventional procedures. Examples of such appropriate salt-forming acids include, for instance, inorganic acids resulting in forming salts such as, but not limited to, hydrohalides (e.g. hydrochloride and hydrobromide), sulfate, nitrate, phosphate, diphosphate, carbonate, bicarbonate, and the like; and organic mono- or di-acids resulting in forming salts such as, for example, acetate, propanoate, hydroxyacetate, 2-hydroxypropanoate, 2-oxo-propanoate, lactate, pyruvate, oxalate, malonate, succinate, maleate, fumarate, malate, tartrate, citrate, methanesulfonate, ethanesulfonate, benzoate, 2-hydroxybenzoate, 4-amino-2-hydroxybenzoate, benzene-sulfonate, p-toluenesulfonate, salicylate, p-amino-salicylate, pamoate, bitartrate, camphor-sulfonate, edetate, 1,2-ethanedisulfonate, fumarate, gluco-heptonate, gluconate, glutamate, hexylresorcinate, hydroxynaphthoate, hydroxyethanesulfonate, mandelate, methylsulfate, pantothenate, stearate, as well as salts derived from ethanedioic, propanedioic, butanedioic, (Z)-2-butene-dioic, (E)2-butenedioic, 2-hydroxybutanedioic, 2,3-dihydroxybutane-dioic, 2-hydroxy-1,2,3-propanetricarboxylic and cyclohexanesulfamic acids and the like.

Trisubstituted pyrido(3,2-d)pyrimidine derivatives represented by the general formula (I), especially these wherein $R_3$ is not halogen, as well as other individual species of tri-substituted pyrido(3,2-d)pyrimidines of this invention, having acidic properties may be converted in a similar manner into the corresponding therapeutically active, non-toxic base addition salt form. Examples of appropriate salt-forming bases include, for instance, inorganic bases like metallic hydroxides such as, but not limited to, those of alkali and alkaline-earth metals like calcium, lithium, magnesium, potassium and sodium, or zinc, resulting in the corresponding metal salt; organic bases such as, but not limited to, ammonia, alkylamines, benzathine, hydrabamine, arginine, lysine, N,N'-dibenzylethylenediamine, chloroprocaine, choline, diethanolamine, ethylene-diamine, N-methylglucamine, procaine and the like.

Reaction conditions for treating the trisubstituted pyrido (3,2-d)pyrimidine derivatives having the general formula (I), as well as other individual species of tri-substituted pyrido(3, 2-d)pyrimidines of this invention, with an appropriate salt-forming acid or base are similar to standard conditions involving the same acid or base but different organic compounds with basic or acidic properties, respectively. Preferably, in view of its use in a pharmaceutical composition or in the manufacture of a medicament for treating specific diseases, the pharmaceutically acceptable salt will be designed, i.e. the salt-forming acid or base will be selected so as to impart greater water solubility, lower toxicity, greater stability and/or slower dissolution rate to the pyrido(3,2-d)pyrimidine derivative of this invention.

The present invention further provides the use of a trisubstituted pyrido(3,2-d)-pyrimidine derivative represented by the structural formula (I), especially these wherein $R_3$ is not halogen, as well as other individual species of tri-substituted pyrido(3,2-d)pyrimidines, or a pharmaceutically acceptable salt or a solvate thereof, as a biologically-active ingredient, i.e. active principle, especially as a medicine or for the manufacture of a medicament for the treatment of a Flaviridae viral infection such as, but not limited to, hepatitis C.

The invention further relates to a pharmaceutical composition comprising:
(a) one or more pyrido(3,2-d)pyrimidine derivatives represented by the structural formula (I), wherein $R_3$ is not halogen, and
(b) one or more pharmaceutically acceptable carriers.

In one embodiment, the compounds of the present invention are used in combination with other active therapeutic ingredients or agents. Combinations of the compounds represented by Formula (I) and additional active agents may be selected to treat patients with a viral infection, e.g., HBV, HCV, or HIV infection.

Preferably, the other active therapeutic ingredients or agents preferably are interferons, ribavirin analogs, HCV NS3 protease inhibitors, alpha-glucosidase 1 inhibitors, hepatoprotectants, non-nucleoside inhibitors of HCV, and other drugs for treating HCV, or mixtures thereof.

Combinations of the compounds represented by Formula (I) are typically selected based on the condition to be treated, cross-reactivities of ingredients and pharmaco-properties of the combination. For example, when treating an infection (e.g., HCV), the compositions of the invention may be combined with other active agents (such as those described herein).

Suitable active agents or ingredients which can be combined with the compounds represented by Formula (I) can include interferons, e.g., pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen+actimmune, IFN-omega with DUROS, albuferon, locteron, Albuferon, Rebif, Oral interferon alpha, IFNalpha-2b XL, AVI-005, PEG-Infergen, and Pegylated IFN-beta; ribavirin analogs, e.g., rebetol, copegus, and viramidine (taribavirin); NS5b polymerase inhibitors, e.g., NM-283, valopicitabine, R1626, PSI-6130 (R1656), HCV-796, BILB 1941, XTL-2125, MK-0608, NM-107, R7128 (R4048), VCH-759, PF-868554, and GSK625433; HCV NS3 protease inhibitors, e.g., SCH-503034 (SCH-7), VX-950 (telaprevir), BILN-2065, BMS-605339, and ITMN-191; alpha-glucosidase 1 inhibitors, e.g., MX-3253 (celgosivir) and UT-231B; hepatoprotectants, e.g., IDN-6556, ME 3738, LB-84451, and MitoQ; non-nucleoside inhibitors of HCV, e.g., benzimidazole derivatives, benzo-1,2,4-thiadiazine derivatives, phenylalanine derivatives, GS-9190, A-831, and A-689; and other drugs for treating HCV, e.g., zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

In yet another embodiment, the present application provides pharmaceutical compositions comprising a compound of the present invention, or a pharmaceutically acceptable salt, solvate, and/or ester thereof, in combination with at least one additional active agent, and a pharmaceutically acceptable carrier or exipient.

According to the present invention, the active agent used in combination with the compound of the present invention can be any agent having a therapeutic effect when used in combination with the compound of the present invention. For example, the active agent used in combination with the compound of the present invention can be interferons, ribavirin analogs, HCV NS3 protease inhibitors, alpha-glucosidase 1 inhibitors, hepatoprotectants, non-nucleoside inhibitors of HCV, and other drugs for treating HCV, or mixtures thereof.

In another embodiment, the present application provides pharmaceutical compositions comprising a compound of the present invention, or a pharmaceutically acceptable salt, solvate, and/or ester thereof, in combination with at least one additional active agent selected from the group consisting of interferons, e.g., pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen+actimmune, IFN-omega with DUROS, albuferon, locteron, Albuferon, Rebif, Oral interferon alpha, IFNalpha-2b XL, AVI-005, PEG-Infergen, and Pegylated IFN-beta; ribavirin analogs, e.g., rebetol, copegus, and viramidine (taribavirin); NS5b polymerase inhibitors, e.g., NM-283, valopicitabine, R1626, PSI-6130 (R1656), HCV-796, BILB 1941, XTL-2125, MK-0608, NM-107, R7128 (R4048), VCH-759, PF-868554, and GSK625433; HCV NS3 protease inhibitors, e.g., SCH-503034 (SCH-7), VX-950 (telaprevir), BILN-2065, BMS-605339, and ITMN-191; alpha-glucosidase 1 inhibitors, e.g., MX-3253 (celgosivir) and UT-231B; hepatoprotectants, e.g., IDN-6556, ME 3738, LB-84451, and MitoQ; non-nucleoside inhibitors of HCV, e.g., benzimidazole derivatives, benzo-1,2,4-thiadiazine derivatives, phenylalanine derivatives, GS-9190, A-831, and A-689; and other drugs for treating HCV, e.g., zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

In yet another embodiment, the present application provides a combination pharmaceutical agent comprising:

a) a first pharmaceutical composition comprising a compound of the present invention, or a pharmaceutically acceptable salt, solvate, or ester thereof; and b) a second pharmaceutical composition comprising at least one additional active agent selected from the group consisting of interferons, ribavirin analogs, HCV NS3 protease inhibitors, alpha-glucosidase 1 inhibitors, hepatoprotectants, non-nucleoside inhibitors of HCV, and other drugs for treating HCV, or mixtures thereof.

More specifically, one or more compounds of the present invention may be combined with one or more compounds selected from the group consisting of interferons, e.g., pegylated rIFN-alpha 2b, pegylated rIFN-alpha 2a, rIFN-alpha 2b, rIFN-alpha 2a, consensus IFN alpha (infergen), feron, reaferon, intermax alpha, rIFN-beta, infergen+actimmune, IFN-omega with DUROS, albuferon, locteron, Albuferon, Rebif, Oral interferon alpha, IFNalpha-2b XL, AVI-005, PEG-Infergen, and Pegylated IFN-beta; ribavirin analogs, e.g., rebetol, copegus, and viramidine (taribavirin); NS5b polymerase inhibitors, e.g., NM-283, valopicitabine, R1626, PSI-6130 (R1656), HCV-796, BILB 1941, XTL-2125, MK-0608, NM-107, R7128 (R4048), VCH-759, PF-868554, and GSK625433; HCV NS3 protease inhibitors, e.g., SCH-503034 (SCH-7), VX-950 (telaprevir), BILN-2065, BMS-605339, and ITMN-191; alpha-glucosidase 1 inhibitors, e.g., MX-3253 (celgosivir) and UT-231B; hepatoprotectants, e.g., IDN-6556, ME 3738, LB-84451, and MitoQ; non-nucleoside inhibitors of HCV, e.g., benzimidazole derivatives, benzo-1,2,4-thiadiazine derivatives, phenylalanine derivatives, GS-9190, A-831, and A-689; and other drugs for treating HCV, e.g., zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

It is also possible to combine any compound of the invention with one or more other active agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active agents generally refers to simultaneous or sequential administration of a compound of the invention and one or more other active agents, such that therapeutically effective amounts of the compound of the invention and one or more other active agents are both present in the body of the patient.

Co-administration includes administration of unit dosages of the compounds of the invention before or after administration of unit dosages of one or more other active agents, for example, administration of the compounds of the invention within seconds, minutes, or hours of the administration of one or more other active agents. For example, a unit dose of a compound of the invention can be administered first, followed within seconds or minutes by administration of a unit dose of one or more other active agents. Alternatively, a unit dose of one or more other active agents can be administered first, followed by administration of a unit dose of a compound of the invention within seconds or minutes. In some cases, it may be desirable to administer a unit dose of a compound of the invention first, followed, after a period of hours (e.g. 1-12 hours), by administration of a unit dose of one or more other active agents. In other cases, it may be desirable to administer a unit dose of one or more other active agents first, followed, after a period of hours (e.g. 1-12 hours), by administration of a unit dose of a compound of the invention.

The combination therapy may provide "synergy" or "synergistic effect", i.e. the effect achieved when the active ingredients used together is greater than the sum of the effects that results from using the compounds separately. A synergistic effect may be attained when the active ingredients are: (1)

co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

In still yet another embodiment, the present application provides for methods of inhibiting HCV polymerase in a cell, comprising: contacting a cell infected with HCV with an effective amount of a compound represented by Formula (I), or a pharmaceutically acceptable salt, solvate, and/or ester thereof, whereby HCV polymerase is inhibited.

In still yet another embodiment, the present application provides for methods of inhibiting HCV polymerase in a cell, comprising contacting a cell infected with HCV with an effective amount of a compound represented by Formula (I), or a pharmaceutically acceptable salt, solvate, and/or ester thereof, and at least one additional active agent, whereby HCV polymerase is inhibited.

In still yet another embodiment, the present application provides for methods of inhibiting HCV polymerase in a cell, comprising contacting a cell infected with HCV with an effective amount of a compound represented by Formula (I), or a pharmaceutically acceptable salt, solvate, and/or ester thereof, and at least one additional active agent selected from the group consisting of interferons, ribavirin analogs, HCV NS3 protease inhibitors, alpha-glucosidase 1 inhibitors, hepatoprotectants, non-nucleoside inhibitors of HCV, and other drugs for treating HCV.

In still yet another embodiment, the present application provides for methods of treating a viral infection in a patient, comprising: administering to the patient a therapeutically effective amount of a compound represented by Formula (I), or a pharmaceutically acceptable salt, solvate, and/or ester thereof.

In still yet another embodiment, the present application provides for methods of treating a viral infection in a patient, comprising: administering to the patient a therapeutically effective amount of a compound represented by Formula (I), or a pharmaceutically acceptable salt, solvate, and/or ester thereof, and at least one additional active agent.

In still yet another embodiment, the present application provides for methods of treating HCV in a patient, comprising: administering to the patient a therapeutically effective amount of a compound represented by Formula (I), or a pharmaceutically acceptable salt, solvate, and/or ester thereof.

In still yet another embodiment, the present application provides for methods of treating HCV in a patient, comprising: administering to the patient a therapeutically effective amount of a compound represented by Formula (I), or a pharmaceutically acceptable salt, solvate, and/or ester thereof, and at least one additional active agent, whereby HCV polymerase is inhibited.

In still yet another embodiment, the present application provides for methods of treating HCV in a patient, comprising: administering to the patient a therapeutically effective amount of a compound represented by Formula (I), or a pharmaceutically acceptable salt, solvate, and/or ester thereof, and at least one additional active agent selected from the group consisting of interferons, ribavirin analogs, HCV NS3 protease inhibitors, alpha-glucosidase 1 inhibitors, hepatoprotectants, non-nucleoside inhibitors of HCV, and other drugs for treating HCV, or mixtures thereof.

In still yet another embodiment, the present application provides for the use of a compound of the present invention, or a pharmaceutically acceptable salt, solvate, and/or ester thereof, for the preparation of a medicament for treating a viral infection, e.g., an HBV/HCV infection.

In yet another embodiment, the present application provides a method for treating or preventing a viral infection comprising co-administering, to a patient in need thereof, a therapeutically effective amount of at least one compound represented by Formula (I) and at least one additional active agent selected from the group consisting of interferons, e.g., pegylated rIFN-alpha 2b, pegylated rIFN-alpha 2a, rIFN-alpha 2b, rIFN-alpha 2a, consensus IFN alpha (infergen), feron, reaferon, intermax alpha, rIFN-beta, infergen+actimmune, IFN-omega with DUROS, albuferon, locteron, Albuferon, Rebif, Oral interferon alpha, IFNalpha-2b XL, AVI-005, PEG-Infergen, and Pegylated IFN-beta; ribavirin analogs, e.g., rebetol, copegus, and viramidine (taribavirin); NS5b polymerase inhibitors, e.g., NM-283, valopicitabine, R1626, PSI-6130 (R1656), HCV-796, BILB 1941, XTL-2125, MK-0608, NM-107, R7128 (R4048), VCH-759, PF-868554, and GSK625433; HCV NS3 protease inhibitors, e.g., SCH-503034 (SCH-7), VX-950 (telaprevir), BILN-2065, BMS-605339, and ITMN-191; alpha-glucosidase 1 inhibitors, e.g., MX-3253 (celgosivir) and UT-231B; hepatoprotectants, e.g., IDN-6556, ME 3738, LB-84451, and MitoQ; non-nucleoside inhibitors of HCV, e.g., benzimidazole derivatives, benzo-1,2,4-thiadiazine derivatives, phenylalanine derivatives, GS-9190, A-831, and A-689; and other drugs for treating HCV, e.g., zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

In another more specific embodiment, this invention provides combinations, preferably synergistic combinations, of one or more pyrido(3,2-d)pyrimidine derivatives represented by the general formula (I), wherein $R_3$ is not halogen, as well as other individual species of tri-substituted pyrido(3,2-d) pyrimidines of this invention, with one or more antiviral agents. As is conventional in the art, the evaluation of a synergistic effect in a drug combination may be made by analyzing the quantification of the interactions between individual drugs, using the median effect principle described by Chou et al. in *Adv. Enzyme Reg.* (1984) 22:27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon CI<1, CI=1, or CI>1, respectively. As will be explained in more detail herein below, this principle may be applied to a number of biologically desirable effects such as, but not limited to, an anti-viral activity against a Flaviridae virus, e.g. HCV.

The invention further relates to a pharmaceutical composition or combined preparation having synergistic effects against a hepatitis C infection and containing:
(a) one or more anti-viral agents, and
(b) at least one pyrido(3,2-d)pyrimidine derivative represented by the general formula (I), wherein $R_3$ is not halogen, and
(c) optionally one or more pharmaceutical excipients or pharmaceutically acceptable carriers,
for simultaneous, separate or sequential use in the treatment of HCV infection.

Suitable anti-viral agents for inclusion into the synergistic antiviral compositions or combined preparations of this invention include, for instance, ribavirin, (pegylated)interferon, and retroviral enzyme inhibitors belonging to categories well known in the art, such as HIV-1 IN inhibitors, nucleoside reverse transcriptase inhibitors (e.g. zidovudine, lamivudine, didanosine, stavudine, zalcitabine and the like), non-nucleoside reverse transcriptase inhibitors (e.g. nevirapine, delavirdine and the like), other reverse transcriptase inhibitors (e.g. foscarnet sodium and the like), and HIV-1 protease inhibitors (e.g. saquinavir, ritonavir, indinavir, nelfinavir and the like). Other suitable antiviral agents include for instance acemannan, acyclovir, adefovir, alovudine, alvircept, amantadine, aranotin, arildone, atevirdine, pyridine, cidofovir, cipamfylline, cytarabine, desciclovir, disoxaril, edoxudine, enviradene, enviroxime, famciclovir, famotine, fiacitabine, fialuridine, floxuridine, fosarilate, fosfonet, ganciclovir, idoxuridine, kethoxal, lobucavir, memotine, methisazone, penciclovir, pirodavir, somantadine, sorivudine, tilorone, trifluridine, valaciclovir, vidarabine, viroxime, zinviroxime, moroxydine, podophyllotoxin, ribavirine, rimantadine, stallimycine, statolon, tromantadine and xenazoic acid, and their pharmaceutically acceptable salts.

Especially relevant to this aspect of the invention is the inhibition of the replication of viruses selected from the group consisting of picorna-, toga-, bunya, orthomyxo-, paramyxo-, rhabdo-, retro-, arena-, hepatitis B-, hepatitis C-, hepatitis D-, adeno-, vaccinia-, papilloma-, herpes-, corona-, varicella- and zoster-virus, in particular human immunodeficiency virus (HIV). Synergistic activity of the pharmaceutical compositions or combined preparations of this invention against viral infection may be readily determined by means of one or more tests such as, but not limited to, the isobologram method, as previously described by Elion et al. in *J. Biol. Chem.* (1954) 208:477-488 and by Baba et al. in *Antimicrob. Agents Chemother.* (1984) 25:515-517, using $EC_{50}$ for calculating the fractional inhibitory concentration (hereinafter referred as FIC). When the minimum FIC index corresponding to the FIC of combined compounds (e.g., $FIC_x+FIC_y$) is equal to 1.0, the combination is said to be additive; when it is between 1.0 and 0.5, the combination is defined as sub-synergistic, and when it is lower than 0.5, the combination is by defined as synergistic. When the minimum FIC index is between 1.0 and 2.0, the combination is defined as subantagonistic and, when it is higher than 2.0, the combination is defined as antagonistic.

The pharmaceutical composition or combined preparation with synergistic activity against viral infection according to this invention may contain the trisubstituted pyrido(3,2-d) pyrimidine derivative represented by the structural formula (I), wherein $R_3$ is not halogen, over a broad content range depending on the contemplated use and the expected effect of the preparation. The trisubstituted pyrido(3,2-d)pyrimidine derivative content of the combined preparation may be within a range of from about 1 to about 99% by weight, preferably from about 5 to about 95% by weight, more preferably from about 20 to 80% by weight.

The pharmaceutical compositions and combined preparations according to this invention may be administered orally or in any other suitable fashion. Oral administration is preferred and the preparation may have the form of a tablet, aqueous dispersion, dispersable powder or granule, emulsion, hard or soft capsule, syrup, elixir or gel. The dosing forms may be prepared using any method known in the art for manufacturing these pharmaceutical compositions and may comprise as additives sweeteners, flavoring agents, coloring agents, preservatives and the like. Carrier materials and excipients are detailed hereinbelow and may include, inter alia, calcium carbonate, sodium carbonate, lactose, calcium phosphate or sodium phosphate; granulating and disintegrating agents, binding agents and the like. The pharmaceutical composition or combined preparation of this invention may be included in a gelatin capsule mixed with any inert solid diluent or carrier material, or has the form of a soft gelatin capsule, in which the ingredient is mixed with a water or oil medium. Aqueous dispersions may comprise the biologically active composition or combined preparation in combination with a suspending agent, dispersing agent or wetting agent. Oil dispersions may comprise suspending agents such as a vegetable oil. Rectal administration is also applicable, for instance in the form of suppositories or gels. Injection (e.g. intramuscularly or intraperiteneously) is also applicable as a mode of administration, for instance in the form of injectable solutions or dispersions, depending upon the disorder to be treated and the condition of the patient.

The term "pharmaceutically acceptable carrier or excipient" as used herein in relation to pharmaceutical compositions and combined preparations means any material or substance with which the active principle, i.e. the trisubstituted pyrido(3,2-d)pyrimidine derivative represented by the general formula (I), wherein $R_3$ is not halogen, as well as another individual species of tri-substituted pyrido(3,2-d)pyrimidines of this invention, and optionally the additional one or more antiviral agents, may be formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders.

Suitable pharmaceutical carriers for use in the said pharmaceutical compositions and their formulation are well known to those skilled in the art. There is no particular restriction to their selection within the present invention although, due to the usually low or very low water-solubility of the trisubstituted pyrido(3,2-d)pyrimidine derivatives of this invention, special attention will be paid to the selection of suitable carrier combinations that can assist in properly formulating them in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals.

The pharmaceutical compositions of the present invention may be prepared in any known manner, for instance by homogeneously mixing, dissolving, spray-drying, coating and/or grinding the active ingredients, in a one-step or a multi-steps procedure, with the selected carrier material and, where appropriate, the other additives such as surface-active agents. may also be prepared by micronisation, for instance in view to obtain them in the form of microspheres usually having a diameter of about 1 to 10 µm, namely for the manufacture of microcapsules for controlled or sustained release of the biologically active ingredient(s).

Suitable surface-active agents to be used in the pharmaceutical compositions of the present invention are non-ionic, cationic and/or anionic surfactants having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alkanolamine salts of dodecylbenzene sulphonic acid or dibutyl-naphthalenesulphonic acid or a naphtalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanyl-phosphatidylcholine, dipalmitoylphosphatidylcholine and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with polypropylene glycol, ethylenediamino-polypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having four hydrocarbon radicals optionally substituted with halo, phenyl, substituted phenyl or hydroxy; for instance quaternary ammonium salts containing as N-substituent at least one $C_8$-$C_{22}$ alkyl radical (e.g. cetyl, lauryl, palmityl, myristyl, oleyl and the like) and, as further substituents, unsubstituted or halogenated lower alkyl, benzyl and/or hydroxy-$C_{1-4}$ alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", $2^{nd}$ ed. (Hanser Verlag, Vienna, 1981) and "Encyclopaedia of Surfactants (Chemical Publishing Co., New York, 1981).

Structure-forming, thickening or gel-forming agents may be included into the pharmaceutical compositions and combined preparations of the invention. Suitable such agents are in particular highly dispersed silicic acid, such as the product commercially available under the trade name Aerosil; bentonites; tetraalkyl ammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antisettle).

Gelling agents which may be included into the pharmaceutical compositions and combined preparations of the present invention include, but are not limited to, cellulose derivatives such as carboxymethylcellulose, cellulose acetate and the like; natural gums such as arabic gum, xanthum gum, tragacanth gum, guar gum and the like; gelatin; silicon dioxide; synthetic polymers such as carbomers, and mixtures thereof. Gelatin and modified celluloses represent a preferred class of gelling agents.

Other optional excipients which may be included in the pharmaceutical compositions and combined preparations of the present invention include additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzylalcohol, methyl paraben, propyl paraben and the like; sequestering agents such as ethylene-diamine tetraacetic acid; flavoring agents such as natural vanillin; buffers such as citric acid and acetic acid; extenders or bulking agents such as silicates, diatomaceous earth, magnesium oxide or aluminum oxide; densification agents such as magnesium salts; and mixtures thereof.

Additional ingredients may be included in order to control the duration of action of the biologically-active ingredient in the compositions and combined preparations of the invention. Control release compositions may thus be achieved by selecting appropriate polymer carriers such as for example polyesters, polyamino-acids, polyvinyl-pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethyl-cellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition or combined preparation of the invention may also require protective coatings.

Pharmaceutical forms suitable for injectable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol, complexing agents such as cyclodextrins and the like, and mixtures thereof.

Other modes of local drug administration can also be used. For example, the selected active agent may be administered topically, in an ointment, gel or the like, or transdermally, using a conventional transdermal drug delivery system.

Since, in the case of combined preparations including a trisubstituted pyrido(3,2-d)pyrimidine derivative of this invention and an additional antiviral agent, both ingredients do not necessarily bring out their synergistic therapeutic effect against the pathologic condition (viral infection) directly at the same time in the patient to be treated, the said combined preparation may be in the form of a medical kit or package containing the two ingredients in separate but adjacent form. In the latter context, each ingredient may therefore be formulated in a way suitable for an administration route different from that of the other ingredient, e.g. one of them may be in the form of an oral or parenteral formulation whereas the other is in the form of an ampoule for intravenous injection or an aerosol.

The present invention further relates to a method for treating hepatitis C in a patient, preferably a mammal, more preferably a human being. The method of this invention consists of administering to the patient in need thereof an effective amount of a trisubstituted pyrido(3,2-d)pyrimidine derivative represented by the general formula (I), wherein $R_3$ is not halogen, or another individual species of tri-substituted pyrido(3,2-d)pyrimidines of this invention, optionally together with an effective amount of an antiviral agent, or a pharmaceutical composition comprising the same, such as disclosed above in extensive details. The effective amount is usually in the range of about 0.01 mg to 20 mg, preferably about 0.1 mg to 5 mg, per day per kg bodyweight for humans. Depending upon the pathologic condition to be treated and the patient's condition, the said effective amount may be divided into several sub-units per day or may be administered at more than one day intervals. The patient to be treated may be any warm-blooded animal, preferably a mammal, more preferably a human being, suffering from said pathologic condition.

The preferred compounds of the present invention are non-sedating. In other words, a dose of such compounds that is twice the minimum dose sufficient to provide analgesia in an animal model for determining pain relief causes only transient (i.e. lasting for no more than half the time that pain relief lasts) or preferably no statistically significant sedation in an animal model assay of sedation (using the method described by Fitzgerald et al. in *Toxicology* (1988) 49:433-9). Preferably, a dose that is five times the minimum dose sufficient to provide analgesia does not produce statistically significant sedation. More preferably, a compound provided herein does not produce sedation at intravenous doses of less than 10 mg/kg per day or at oral doses of less than 30 mg/kg per day. If desired, compounds provided herein may be evaluated for toxicity (a preferred compound is non-toxic when an antiviral amount is administered to a subject) and/or side effects (a preferred compound produces side effects comparable to placebo when a therapeutically effective amount of the compound is administered to a subject). Toxicity and side effects may be assessed using any standard method. In general, the term "non-toxic" as used herein shall be understood as referring to any substance that, in keeping with established criteria, is susceptible to approval by the United States Federal Drug Administration for administration to mammals, preferably humans. Toxicity may be also evaluated using assays including bacterial reverse mutation assays, such as an Ames test, as well as standard teratogenicity and tumorogenicity assays. Preferably, administration of compounds provided herein within the therapeutic dose ranges disclosed hereinabove does not result in prolongation of heart QT intervals (e.g. as determined by electrocardiography in guinea pigs, minipigs or dogs). When administered daily, such doses also do not cause liver enlargement resulting in an increase of liver to body weight ratio of more than 50% over matched controls in laboratory rodents (e.g. mice or rats). Such doses also preferably do not cause liver enlargement resulting in an increase of liver to body weight ratio of more than 10% over matched untreated controls in dogs or other non-rodent mammals.

Another embodiment of this invention includes the various precursors or "pro-drug" forms of the trisubstituted pyrido(3,2-d)pyrimidine derivatives having the general formula (I), wherein $R_3$ is not halogen, of the present invention. It may be desirable, under specific circumstances, to formulate the compounds of the present invention in the form of a chemical species which itself is not significantly biologically-active, but which when delivered to the body of a human being or higher mammal will undergo a chemical reaction catalyzed by the normal function of the body, inter alia, enzymes present in the stomach or in blood serum, said chemical reaction having the effect of releasing a compound as defined herein. The term "pro-drug" thus relates to these species which are converted in vivo into the active pharmaceutical ingredient.

The pro-drugs of the present invention can have any form suitable to the formulator, for example, esters are non-limiting common pro-drug forms. In the present case, however, the pro-drug may necessarily exist in a form wherein a covalent bond is cleaved by the action of an enzyme present at the target locus. For example, a C—C covalent bond may be selectively cleaved by one or more enzymes at said target locus and, therefore, a pro-drug in a form other than an easily hydrolysable precursor, inter alia an ester, an amide, and the like, may be used.

For the purpose of the present invention the term "therapeutically suitable pro-drug" is defined herein as a compound modified in such a way as to be transformed in vivo to the therapeutically active form, whether by way of a single or by multiple biological transformations, when in contact with the tissues of humans or mammals to which the pro-drug has been administered, and without undue toxicity, irritation, or allergic response, and achieving the intended therapeutic outcome.

The present invention will be further described with reference to certain more specific embodiments, detailed schemes and examples, but the present invention is not limited thereto but only by the attached claims. The following examples are given by way of illustration only.

Example 1

Synthesis of 2-amino-6-(4-fluorophenyl)-pyrido(3,2-d)pyrimidin-4(3H)thione

A suspension of 2-amino-6-(4-fluorophenyl)-pyrido(3,2-d)pyrimidin-4(3H)one (2.56 g) and phosphorus pentasulfide (2.5 g) in pyridine (200 ml) was refluxed for 4 hours. The reaction mixture was cooled down and the precipitate was filtered off, thus providing 2.0 g (yield: 73%) of the pure title compound, which was characterized by its mass spectrum as follows: MS (m/z): 273 ([M+H]$^+$, 100).

Example 2

Synthesis of 2-amino-4-methylthio-6-(4-fluorophenyl)-pyrido(3,2-d)pyrimidine

To a solution of the 2-amino-6-(4-fluorophenyl)-pyrido(3,2-d)pyrimidin-4(3H)thione from example 1 (55 mg) in a 1 N NaOH solution (10 ml) was added methyl iodide (0.2 mmole). The reaction mixture was stirred at room temperature for 12 hours, then diluted with diethyl ether and the organic layer was extracted with water. The combined organic layers were evaporated in vacuo and the crude residue was purified by preparative thin layer chromatography on silica, the mobile phase being a mixture of methanol and dichloromethane, in a volume ratio of 5:95, providing 41 mg of the pure title compound (yield 72%) which was characterized by its mass spectrum as follows: MS (m/z): 287 ([M+H]$^+$, 100).

Examples 3 to 14

Synthesis of 2-amino-4-substituted-6-(4-fluorophenyl)-pyrido(3,2-d) pyrimidines

To a solution of the 2-amino-4-thiomethyl-6-(4-fluorophenyl)-pyrido(3,2-d)pyrimidine of example 2 (56 mg) in a suitable alcohol (5 ml) was added a 2 M solution of lithium diisopropylamide (LDA) in tetrahydrofuran (1 ml). The reaction mixture was stirred at room temperature for 3 days. The excess alcohol was evaporated in vacuo and the crude residue was purified by preparative thin layer chromatography on silica using a mixture of toluene and acetonitrile as the mobile phase (in a volume ratio of 1:1). If necessary a second purification was performed by HPLC on a C18-RP column (100× 30 mm Gemini 5 μm) with a gradient of H$_2$O, 0.05% TEA-acetonitrile. The resulting compounds were isolated in yields varying from 30 to 50%, depending on the alcohol used, and were characterized by their mass spectra MS as indicated below.

2-amino-4-(2-propoxyethoxy)-6-(4-fluorophenyl)pyrido(3,2-d)pyrimidine (example 3) was obtained from 2-propoxyethanol; MS (m/z): 343 ([M+H]$^+$, 100).

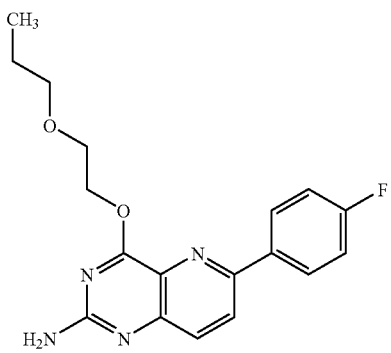 [SMILES: CCCOCCOc1nc(N)nc2ccc(-c3ccc(F)cc3)nc12]

2-amino-4-(2-butoxyethoxy)-6-(4-fluorophenyl)pyrido(3,2-d)pyrimidine (example 4) was obtained from 2-butoxyethanol; MS (m/z): 357 ([M+H]$^+$, 100).

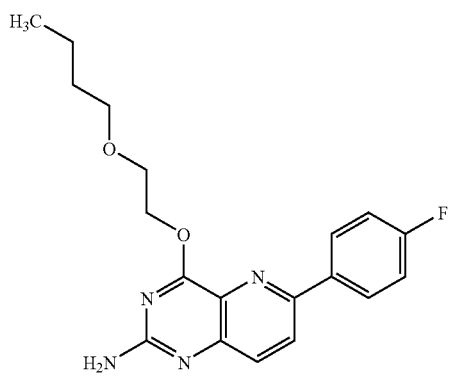 [SMILES: CCCCOCCOc1nc(N)nc2ccc(-c3ccc(F)cc3)nc12]

2-amino-4-(2-ethoxy-1-propoxy)-6-(4-fluorophenyl)pyrido(3,2-d)pyri-midine (example 5) was obtained from 2-ethoxy-1-propanol; MS (m/z): 343 ([M+H]$^+$, 100).

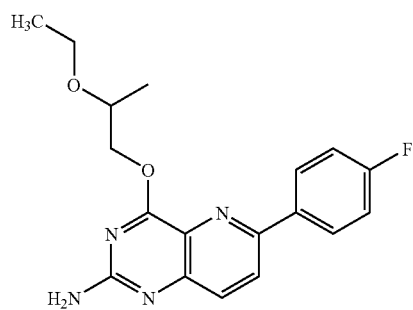 [SMILES: CCOC(C)COc1nc(N)nc2ccc(-c3ccc(F)cc3)nc12]

2-amino-4-(2-isopropoxyethoxy)-6-(4-fluorophenyl)pyrido(3,2-d)pyrimidine (example 6) was obtained from 2-isopropoxyethanol; MS (m/z): 343 ([M+H]$^+$, 100).

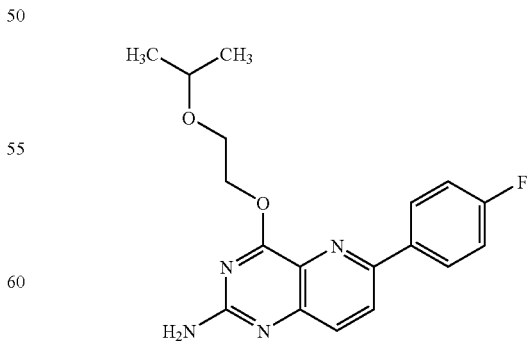

2-amino-4-(2,2-difluoroethoxy)-6-(4-fluorophenyl)pyrido(3,2-d)pyrimidine (example 7) was obtained from 2,2-difluoroethanol; MS (m/z): 321 ([M+H]$^+$, 100)

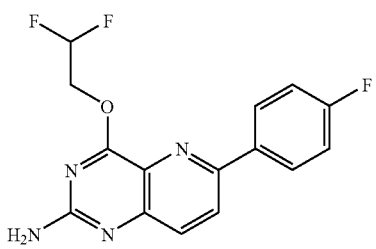 [SMILES: Nc1nc(OCC(F)F)c2nc(-c3ccc(F)cc3)ccc2n1]

2-amino-4-[2-(methylthio)ethoxy]-6-(4-fluorophenyl)py-rido(3,2-d)pyrimidine (example 8) was obtained from 2-(methylthio)ethanol; MS (m/z): 331 ([M+H]$^+$, 100).

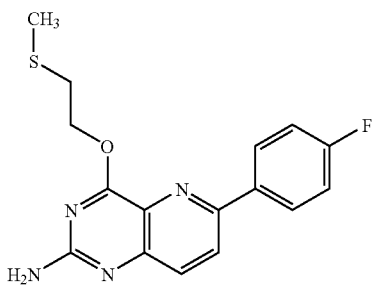 [SMILES: CSCCOc1nc(N)nc2ccc(-c3ccc(F)cc3)nc12]

2-amino-4-(cyclobutoxy)-6-(4-fluorophenyl)pyrido(3,2-d)pyrimidine (example 9) was obtained from cyclobutanol; MS (m/z): 311 ([M+H]$^+$, 100).

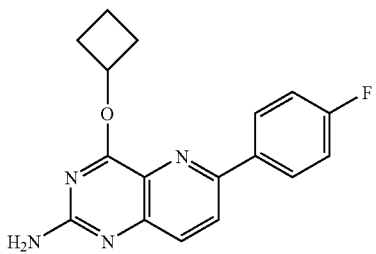 [SMILES: Nc1nc(OC2CCC2)c2nc(-c3ccc(F)cc3)ccc2n1]

2-amino-4-(cyclopentylmethoxy)-6-(4-fluorophenyl)py-rido(3,2-d)pyrimidine (example 10) was obtained from cyclopentanemethanol; MS (m/z): 339 ([M+H]$^+$, 100).

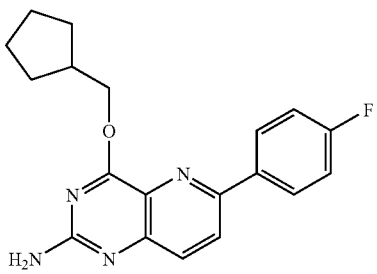 [SMILES: Nc1nc(OCC2CCCC2)c2nc(-c3ccc(F)cc3)ccc2n1]

2-amino-4-(cyclopentoxy)-6-(4-fluorophenyl)pyrido(3,2-d)pyrimidine (example 11) was obtained from cyclopentanol; MS (m/z): 325 ([M+H]$^+$, 100).

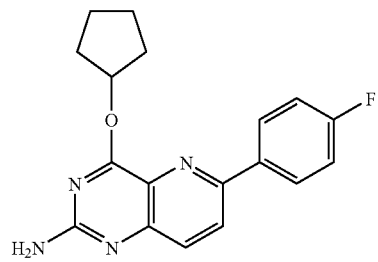 [SMILES: Nc1nc(OC2CCCC2)c2nc(-c3ccc(F)cc3)ccc2n1]

2-amino-4-(3-methyl-3-methoxybutoxy)-6-(4-fluorophenyl)pyrido(3,2-d) pyrimidine (example 12) was obtained from 3-methyl-3-methoxy-butanol; MS (m/z): 357 ([M+H]$^+$, 100).

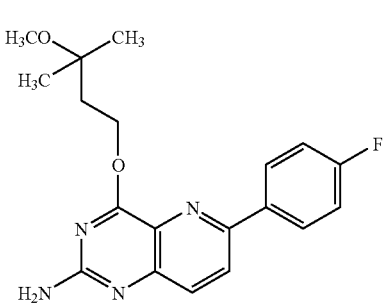 [SMILES: COC(C)(C)CCOc1nc(N)nc2ccc(-c3ccc(F)cc3)nc12]

2-amino-4-(2-methyl-3-buten-2-oxy)-6-(4-fluorophenyl) pyrido(3,2-d)pyrimidine (example 13) was obtained from 2-methyl-3-buten-2-ol; MS (m/z): 325 ([M+H]$^+$, 100).

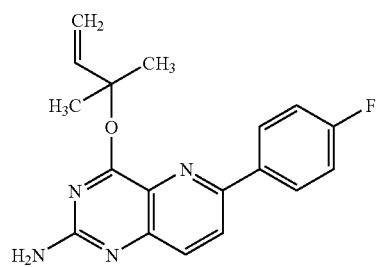 [SMILES: C=CC(C)(C)Oc1nc(N)nc2ccc(-c3ccc(F)cc3)nc12]

2-amino-4-(3-pentyn-1-oxy)-6-(4-fluorophenyl)pyrido(3,2-d)pyrimidine (example 14) was obtained from 3-pentyn-1-ol.

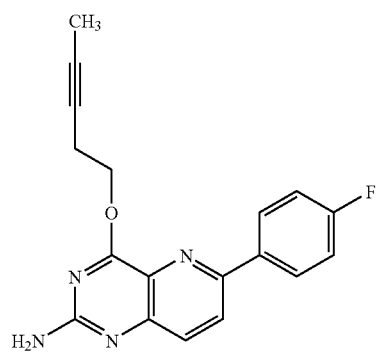 [SMILES: CC#CCCOc1nc(N)nc2ccc(-c3ccc(F)cc3)nc12]

Example 15

Synthesis of 2-amino-4-(1,2,4-triazolyl)-6-(4-fluorophenyl)-pyrido (3,2-d) pyrimidine To a stirred suspension of 2-amino-6-(4-fluorophenyl)-3H-pyrido[3,2-d]pyrimidin-4-one (2.56 g, 10 mmole) and N,N-diisopropylethylamine (3.5 mL, 20 mmol) in acetonitrile (75 mL) was added a suspension of 1,2,4-triazole (1.38 g, 20 mmol) and phosphorus oxychloride (1.8 mL, 20 mmol) in dry acetonitrile (75 mL), portion-wise. The reaction mixture was stirred at ambient temperature for 20 hours. Then to it was added N,N-diisopropylethylamine (3.5 mL, 20 mmol), followed by a suspension of 1,2,4-triazole (1.38 g, 20 mmol) and phosphorus oxychloride (1.8 mL, 20 mmol) in dry acetonitrile (50 mL). The reaction mixture was stirred for 3 days until all the starting material was consumed. The solid was collected by vacuum filtration, washed with small amounts of acetonitrile, dichloromethane and diethyl ether, and then dried under high vacuum for one day to afford 3.18 g of the title compound as a light yellow solid. which was characterized by its mass spectrum as follows: MS (m/z): 308.1 ([M+H]$^+$, 100).

Examples 16 to 24

Synthesis of 2-amino-4-substituted-6-(4-fluorophenyl)pyrido (3,2-d)pyrimidines To a solution of the 2-amino-4-[1,2,4-triazolyl]-6-(4-fluorophenyl)-pyrido(3,2-d)pyri-midine (50 mg) of example 15 and a suitable alcohol (0.2 ml) in DCM (1.5 mL) was added a 1 M solution of potassium tert-butoxide in tetrahydrofuran (0.16 ml). The reaction mixture was heated via microwave to 100° C. for 20 minutes. The solvents ware evaporated in vacuo and the crude residue was purified by HPLC on a C18-RP column (100×30 mm Gemini 5 μm) with a gradient of H$_2$O, 0.05% TEA-acetonitrile. The following resulting compounds were characterized by their mass spectra as follows:

2-amino-4-[3(S)-tetrahydrofuranyloxy]-6-(4-fluorophenyl)-pyrido(3,2-d)pyrimidine (example 16); MS (m/z): 327 ([M+H]$^+$, 100)

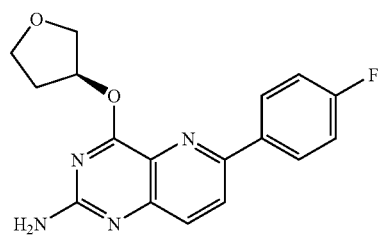 [SMILES: Nc1nc(O[C@H]2CCOC2)c2nc(-c3ccc(F)cc3)ccc2n1]

2-amino-4-[3(R)-tetrahydrofuranyloxy]-6-(4-fluorophenyl)-pyrido(3,2-d) pyrimidine (example 17); MS (m/z): 327 ([M+H]$^+$, 100).

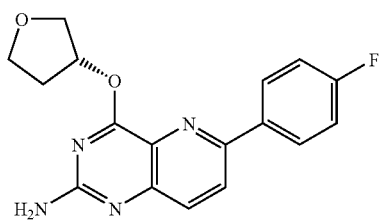

2-amino-4-[hexahydro-furo(2,3-b)furan-3-oxy]-6-(4-fluorophenyl)-pyrido(3,2-d) pyrimidine (example 18) was obtained from hexahydrofuro[2,3-b]furan-3-ol; MS (m/z): 369 ([M+H]$^+$, 100)

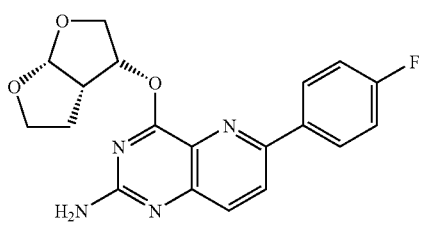

2-amino-4-[2-(methylsulfonyl)ethoxy]-6-(4-fluorophenyl)-pyrido(3,2-d) pyrimidine (example 19) was obtained from 2-(methylsulfonyl)ethanol; MS (m/z): 363 ([M+H]$^+$, 100).

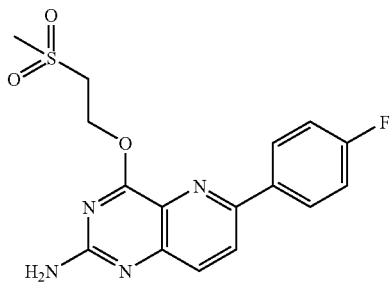 [SMILES: CS(=O)(=O)CCOc1nc(N)nc2ccc(-c3ccc(F)cc3)nc12]

4-(1-ethyl-propoxy)-6-(4-fluoro-phenyl)-pyrido[3,2-d]pyrimidin-2-ylamine (example 20) was obtained from pentan-3-ol; MS (m/z): 327 ([M+H]$^+$, 100).

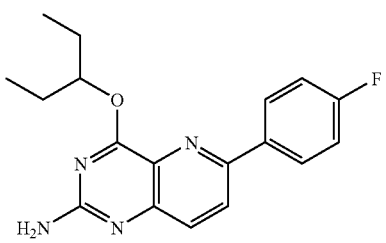 [SMILES: CCC(CC)Oc1nc(N)nc2ccc(-c3ccc(F)cc3)nc12]

6-(4-fluoro-phenyl)-4-(2-morpholin-4-yl-ethoxy)-pyrido [3,2-d]pyrimidin-2-ylamine (example 21) was obtained from, 2-morpholin-4-yl-ethanol; MS (m/z): 370 ([M+H]$^+$, 100).

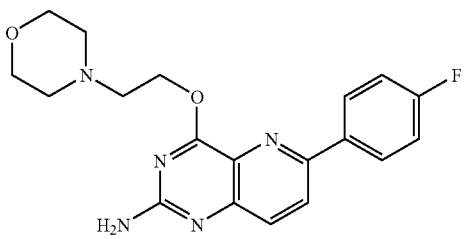 [SMILES: Nc1nc(OCCN2CCOCC2)c2nc(-c3ccc(F)cc3)ccc2n1]

4-cyclopropylmethoxy-6-(4-fluoro-phenyl)-pyrido[3,2-d]pyrimidin-2-ylamine (example 22) was obtained from cyclopropyl-methanol; MS (m/z): 311 ([M+H]$^+$, 100).

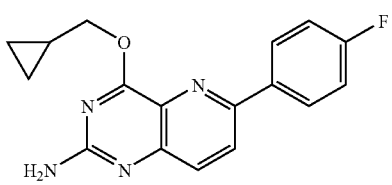 [SMILES: Nc1nc(OCC2CC2)c2nc(-c3ccc(F)cc3)ccc2n1]

6-(4-fluoro-phenyl)-4-(2-methoxy-ethoxy)-pyrido[3,2-d]pyrimidin-2-ylamine (example 23) was obtained from 2-methoxy-ethanol; MS (m/z): 315 ([M+H]$^+$, 100).

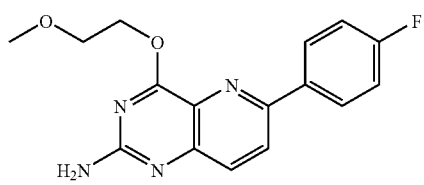 [SMILES: COCCOc1nc(N)nc2ccc(-c3ccc(F)cc3)nc12]

4-(2-ethoxy-ethoxy)-6-(4-fluoro-phenyl)-pyrido[3,2-d]pyrimidin-2-ylamine (example 24) was obtained from 2-ethoxy-ethanol; MS (m/z): 329 ([M+H]$^+$, 100).

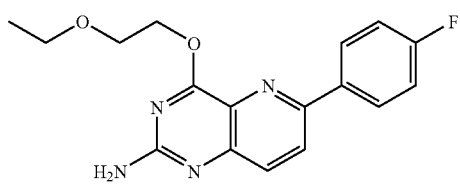 [SMILES: CCOCCOc1nc(N)nc2ccc(-c3ccc(F)cc3)nc12]

Examples 25 to 31

Synthesis of 2-acetamido-4-substituted-6-chloro-pyrido(3,2-d)pyrimidines

To a mixture of 2-acetamido-6-chloro-pyrido[3,2-d]pyrimidin-4(3H)-one (0.72 g), triphenylphosphine (1.18 g), and an appropriate alcohol (4.5 mmole) in CH$_2$Cl$_2$ (50 ml) was added diisopropyl azodicarboxylate (0.91 g). The final mixture was stirred at room temperature for 24 hours and evaporated in vacuo. The residue was chromatographed on silica gel (50 g, flash chromatography) by eluting with CH$_2$Cl$_2$/MeOH (0→5% MeOH by volume). Evaporation of appropriate fractions provided the desired 2-acetamido-4-substituted-6-chloropyrido[3,2-d]pyrimidines with the yields indicated below. These compounds were also characterised with their melting point (m.p.), proton magnetic resonance spectrum, and/or elemental analysis as follows:

2-acetamido-4-cyclohexyloxy-6-chloro-pyrido(3,2-d)pyrimidine (example 25) was obtained (yield: 29%) from cyclohexanol.

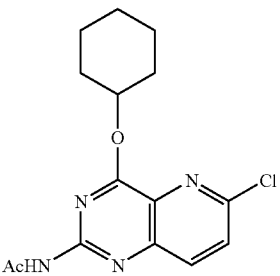 [SMILES: CC(=O)Nc1nc(OC2CCCCC2)c2nc(Cl)ccc2n1]

m.p. 184° C.;

$^1$H NMR (DMSO-d$_6$): δ 10.60 (s, 1H), 8.09 and 7.87 (1H), 5.31 (m, 1H), 2.28 (s, 3H), 2.11 (m, 2H), 1.80 (m, 2H), 1.60 (m, 3H), and 1.36 (m, 3H) ppm; and C$_{15}$H$_{17}$ClN$_4$O$_2$, 0.5H$_2$O (329.78): C, 54.62; H, 5.23; N, 17.22.

2-acetamido-4-(tetrahydro-2H-pyran-4-oxy)-6-chloro-pyrido(3,2-d)pyri-midine (example 26) was obtained (yield: 59%) from tetrahydro-2H-pyran-4-ol.

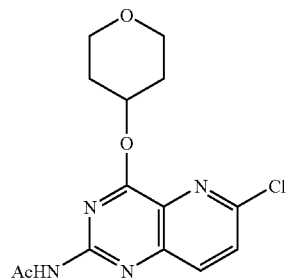 [SMILES: CC(=O)Nc1nc(OC2CCOCC2)c2nc(Cl)ccc2n1]

m.p. 230° C.

$^1$H NMR (DMSO-d$_6$): δ 10.65 (s, 1H), 8.10 and 7.88 (1H), 5.43 (m, 1H), 3.95 and 3.50 (2H), 2.27 (s, 3H), 2.17 and 1.79 (2H) ppm.

C$_{14}$H$_{15}$ClN$_4$O$_3$ (322.75): C, 51.82; H, 4.71; N, 17.33.

2-acetamido-4-(tetrahydropyran-2-methoxy)-6-chloro-pyrido(3,2-d) pyrimidine (example 27) was obtained (yield: 49%) from tetrahydropyran-2-methanol

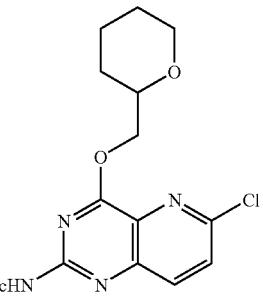

m.p. 193° C.;
$^1$H NMR (DMSO-d$_6$): δ 10.65 (s, 1H), 8.12 and 7.89 (1H), 4.49 (d, 2H), 3.86 (m, 2H), 3.41 (m, 1H), 2.27 (s, 3H), and 1.90-1.19 (m, 6H) ppm.
C$_{15}$H$_{17}$ClN$_4$O$_3$ (336.78): C, 53.10; H, 5.26; N, 16.31.

2-acetamido-4-(tetrahydro-2-furanmethoxy)-6-chloro-pyrido(3,2-d) pyrimidine (example 28) was obtained (yield: 52%) from 2-tetrahydrofuranylmethanol.

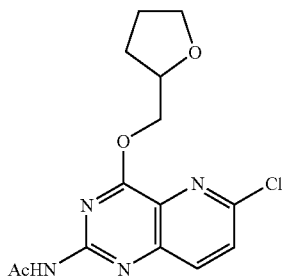 [SMILES: CC(=O)Nc1nc(OCC2CCCO2)c2nc(Cl)ccc2n1]

m.p. 182° C. (MeOH);
$^1$H NMR (DMSO-d$_6$): δ 10.65 (s, 1H), 8.12 and 7.89 (1H), 4.53 (m, 2H), 4.33 (m, 1H), 3.83 (m, 1H), 3.70 (m, 1H), 2.27 (s, 3H), and 2.15-1.60 (m, 4H) ppm; and
C$_{14}$H$_{15}$ClN$_4$O$_3$ (322.75): C, 52.17; H, 4.89; N, 17.35.

2-acetamido-4-(tetrahydro-3-tetrahydrofuranmethoxy)-6-chloro-pyrido-(3,2-d)pyrimidine (example 29) was obtained (yield: 67%) from 3-tetrahydrofuranylmethanol

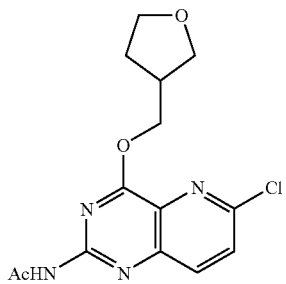 [SMILES: CC(=O)Nc1nc(OCC2CCOC2)c2nc(Cl)ccc2n1]

m.p. 158° C.;
$^1$H NMR (DMSO-d$_6$): δ 10.64 (s, 1H), 8.11 and 7.88 (1H), 4.50 (m, 2H), 3.80 (m, 2H), 3.61 (m, 2H), 2.86 (m, 1H), 2.27 (s, 3H), 2.06 and 1.70 (1H) ppm.
C$_{14}$H$_{15}$ClN$_4$O$_3$ (322.75): C, 52.20; H, 4.68; N, 17.49.

2-acetamido-4-[(S)-1-methoxy-2-propoxy]-6-chloro-pyrido(3,2-d) pyrimidine (example 30) was obtained (yield: 55%) from(S)-1-methoxy-2-propanol.

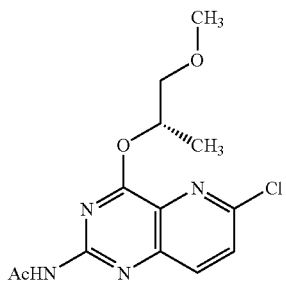 [SMILES: COC[C@H](C)Oc1nc(NC(C)=O)nc2ccc(Cl)nc12]

m.p. 161° C. (MeOH).
$^1$H NMR (DMSO-d$_6$): δ 10.65 (s, 1H), 8.11 and 7.88 (1H), 5.68 (m, 1H), 3.64 (m, 2H), 3.31 (s, 3H), 2.26 (s, 3H), and 1.38 (d, 3H) ppm. C$_{13}$H$_{15}$ClN$_4$O$_3$ (310.75): C, 49.99; H, 4.65; N, 17.89.

2-acetamido-4-[(R)-1-methoxy-2-propoxy]-6-chloro-pyrido(3,2-d)pyri-midine (example 2031) was obtained (yield: 55%) from (R)-1-methoxy-2-propanol.

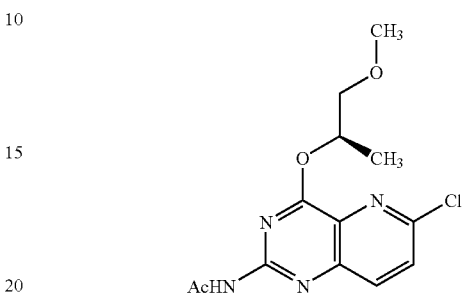

m.p. 160° C. (MeOH).
$^1$H NMR (DMSO-d$_6$): δ 10.66 (s, 1H), 8.11 and 7.88 (1H), 5.68 (m, 1H), 3.64 (m, 2H), 3.31 (s, 3H), 2.26 (s, 3H), and 1.38 (d, 3H) ppm.
C$_{13}$H$_{15}$ClN$_4$O$_3$ (310.75): C, 50.66; H, 5.15; N, 17.96.

Examples 32 to 38

Synthesis of 2-amino-4-substituted-6-(4-fluorophenyl-pyrido(3,2-d) pyrimidines

To a degassed suspension of a 2-acetamido-4-substituted-6-chloro-pyrido[3,2-d]pyrimidine from one of examples 25 to 31 (0.5 mmole), 4-fluorophenylboronic acid (0.55 mmole) and potassium carbonate (2-4 mmole) in a mixture of dioxane (7 ml) and water (2.5 ml) was added tetrakis(triphenyl-phosphine)palladium(0) (0.025 mmole) and the resulting mixture was refluxed at 120° C. for 24 hours. After cooling to room temperature, CH$_2$Cl$_2$ (30 ml) was added and the mixture was washed with brine (10 ml). The organic layer was separated and the water layer was additionally washed with CH$_2$Cl$_2$ 3×5 ml). The combined organic washings were dried (Na$_2$SO$_4$), and evaporated in vacuo. The residue was chromatographed on silica gel (flash chromatography) by eluting with CH$_2$Cl$_2$/MeOH (0→5% MeOH by volume). Evaporation of the appropriate fractions provided the desired 2-amino-4-oxysubstituted-6-(4-fluorophenyl)-pyrido[3,2-d]pyrimidines with the yields indicated below. These compounds were also characterised by proton magnetic resonance spectrum, melting point and/or elemental analysis as follows.

2-amino-4-cyclohexyloxy-6-(4-fluorophenyl)-pyrido(3,2-d)pyrimidine (example 32) was obtained in 78% yield

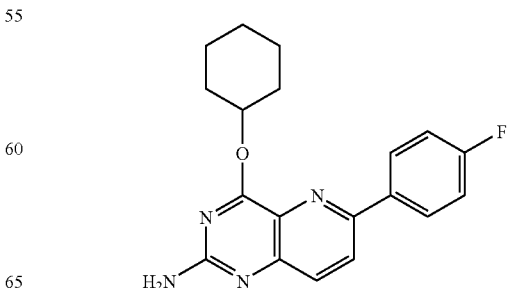

m.p. 180° C.;

¹H NMR (DMSO-d₆): δ 8.19 (m, 3H), 7.75 (d, 1H), 7.35 (t, 2H), 6.84 (s, 2H), 5.31 (s, 1H), and 2.14-1.27 (m, 10H) ppm; and $C_{19}H_{19}FN_4O$ (338.38): C, 67.40; H, 5.89; N, 16.57.

2-amino-4-(tetrahydro-2H-pyran-4-oxy)-6-(4-fluorophenyl)-pyrido(3,2-d)pyrimidine (example 33) was obtained in 59% yield.

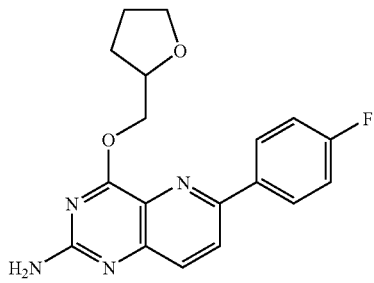

m.p. 193° C.;

¹H NMR (DMSO-d₆): δ 8.20 (m, 3H), 7.77 (d, 1H), 7.35 (t, 2H), 6.93 (s, 2H); 4.47 (m, 2H), 4.34 (m, 1H), 3.86 (m, 1H), 3.71 (m, 1H), and 2.15-1.68 (m, 4H) ppm.

$C_{18}H_{17}FN_4O_2 \times 0.5H_2O$ (349.37): C, 61.75; H, 4.77; N, 16.01.

2-amino-4-(tetrahydro-3-furanmethoxy)-6-(4-fluorophenyl)-pyrido(3,2-d)pyrimidine (example 36) was obtained in 76% yield.

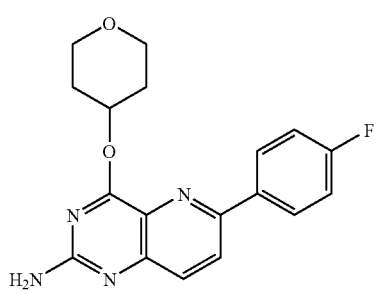 [SMILES: Nc1nc(OC2CCOCC2)c2nc(-c3ccc(F)cc3)ccc2n1]

m.p. 218° C.;

¹H NMR (DMSO-d₆): δ 8.22 (m, 3H), 7.77 (d, 1H), 7.35 (t, 2H), 6.88 (s, 2H), 5.47 (s, 1H); 3.95 and 3.56 (2H), 2.11 and 1.80 (2H) ppm;

$C_{19}H_{19}FN_4O_2$ (340.35): C, 63.59; H, 5.43; N, 16.36.

2-amino-4-(tetrahydropyran-2-methoxy)-6-(4-fluorophenyl)-pyrido(3,2-d)pyrimidine (example 34) was obtained in 77% yield.

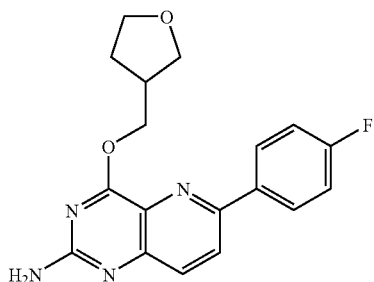

m.p. 219° C.;

¹H NMR (DMSO-d₆): δ 8.20 (m, 3H), 7.77 (d, 1H), 7.35 (t, 2H), 6.91 (s, 2H); 4.45 (m, 2H), 3.85 (m, 2H), 3.68 (m, 2H), 2.83 (1H), 2.07 and 1.75 (1H) ppm; and $C_{18}H_{17}FN_4O_2$ (340.13): C, 62.85; H, 5.23; N, 16.36.

2-amino-4-[(S)-1-methoxy-2-propoxy]-6-(4-fluorophenyl)-pyrido(3,2-d)pyrimidine (example 37) was obtained in 57% yield.

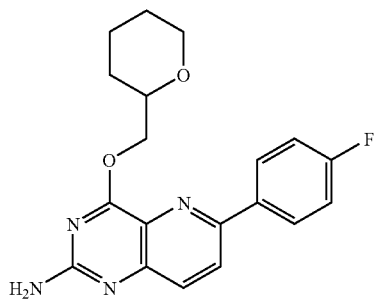 [SMILES: Nc1nc(OCC2CCCCO2)c2nc(-c3ccc(F)cc3)ccc2n1]

m.p. 202° C.;

¹H NMR (DMSO-d₆): δ 8.18 (m, 3H), 7.77 (d, 1H), 7.36 (t, 2H), 6.92 (s, 2H); 4.45 (m, 2H), 3.85 (m, 2H), 3.40 (m, 1H), and 1.92-1.29 (m, 6H) ppm.

$C_{19}H_{19}FN_4O_2 \times 0.5H_2O$ (363.39): C, 62.90; H, 5.46; N, 15.45.

2-amino-4-(tetrahydro-2-furanmethoxy)-6-(4-fluorophenyl)-pyrido(3,2-d)pyrimidine (example 35) was obtained in 57% yield.

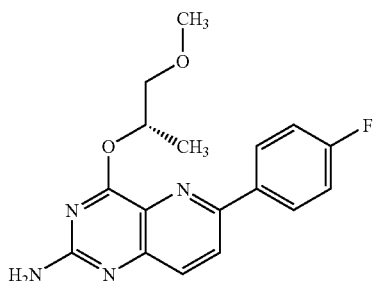

¹H NMR (DMSO-d₆): δ 8.17 (m, 3H), 7.77 (d, 1H), 7.35 (t, 2H), 6.89 (s, 2H); 5.64 (m, 1H), 3.63 (m, 2H), 3.35 (s, 3H), and 1.37 (d, 3H) ppm; and $C_{17}H_{17}FN_4O_2$ (328.34): C, 62.23; H, 5.60; N, 17.06.

2-amino-4-[(R)-1-methoxy-2-propoxy]-6-(4-fluorophenyl)-pyrido(3,2-d)pyrimidine (example 38) was obtained in 73% yield.

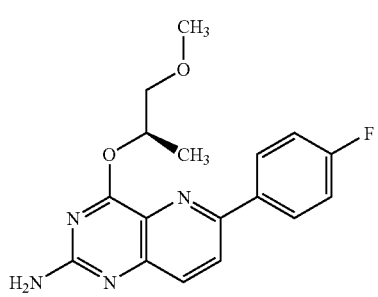 [SMILES: COC[C@@H](C)Oc1nc(N)nc2ccc(-c3ccc(F)cc3)nc12]

$^1$H NMR (DMSO-d$_6$): δ 8.17 (m, 3H), 7.77 (d, 1H), 7.35 (t, 2H), 6.90 (s, 2H); 5.64 (m, 1H), 3.63 (m, 2H), 3.35 (s, 3H), and 1.37 (d, 3H) ppm.

C$_{17}$H$_{17}$FN$_4$O$_2$ (328.34): C, 62.35; H, 5.12; N, 16.72.

Example 39

Anti-HCV Assay/Replicon Assay

The anti-HCV activity of the pyrido[3,2-d]pyrimidine derivatives of this invention was tested in a human hepatoma Huh-7 cell line harbouring a HCV replicon. The assay comprised the following steps:

Step 1: Compound Preparation and Serial Dilution
1. for water soluble pyrido[3,2-d]pyrimidine derivatives, a volume of 500 μL of solution in cell media (DMEM, 10% FBS, P/S, L-Glutamine) was prepared with a concentration being twice the concentration of the starting final serial dilution concentration. A volume of 150 μL of the solution was added to the pre-specified wells in column 1 of a 96-well cell culture plate (PerkinElmer, white plate, cat. #6005181, for EC50 assay; black plate, cat. #6005182 for CC50 assay). The rest of the plate, columns 2-12, was filled with 100 μL of cell media. The plate was then placed on a Precision 2000 Workstation to start the serial dilution. Compounds were diluted three times each step from column 1 to column 10. Column 11 was used as a blank control (no compound added).
2. for pyrido[3,2-d]pyrimidine derivatives requiring DMSO to dissolve, serial dilution is performed in 50% DMSO in a 384-well plate. A solution containing a compound at 100-fold concentration of the starting final serial dilution concentration was prepared in 50% DMSO and added to the pre-specified wells in column 1 of a polypropylene 384-well plate. The plate was then placed on a Precision 2000 Workstation to start the serial dilution. After the serial dilution, a volume of 2 μL of the solution was transferred from the 384-well plate to a 96-well cell culture plate containing 100 μL of cell media on a Biomek FX Workstation. The DMSO concentration in the final assay condition was 0.5% after cells are added to the plate and the total volume in each well is brought to 200 μL.

Step 2: to each well of the serial dilution plate prepared above, 100 μL of cell media containing 6000 suspended Huh-7 HCV replicon cells was added with a Multidrop workstation. The plates were incubated for 3 days at 37° C. with 5% CO$_2$.

Step 3: Detection:
a) for the EC$_{50}$ assay, the media in a 96-well cell culture plate was aspirated with a Biotek EL405 plate-washer. A volume of 200 μL of a solution containing a 1:1 mixture of cell-lysis buffer (Promega, Luciferase Cell Culture Lysis 5× Reagent, cat. #E1531) and luciferase substrate solution (Promega, Luciferase Assay, cat. # E4550) was added to each well of the plate with Multidrop. The plate was incubated for 30 minutes at room temperature before the luminescence signal was measured with a TopCount plate-reader.
b) for the CC$_{50}$ assay, a volume of 100 μL of pre-mixed CellTiter-Glo (Promega, cat. # G7572) solution is added directly to the cell culture in each well of the plate and the luminescence signal is measured with a TopCount plate-reader after 10 minutes of incubation at room temperature.

Table 1 below shows EC$_{50}$ and CC$_{50}$ ranges of derivatives tested in this assay. Results in table 13 are expressed by the following data:
the 50% effective concentration (EC$_{50}$), i.e. the concentration that protects 50% of the cell monolayer from virus-induced cytopathic effect, and
the 50% cytostatic concentration (CC$_{50}$), i.e. the concentration that results in 50% inhibition of cell growth.

TABLE 1

| Example | EC$_{50}$ (A <300 nM; B 300-1,000 nM; C >1,000 nM) | CC$_{50}$ (A <10 μM; B 10-20 μM; C >20 μM) |
|---|---|---|
| 3 | B | C |
| 4 | C | C |
| 5 | A | C |
| 6 | A | C |
| 7 | A | C |
| 8 | A | C |
| 9 | A | C |
| 10 | B | C |
| 11 | A | C |
| 12 | A | C |
| 13 | C | C |
| 14 | C | C |
| 16 | A | C |
| 17 | A | C |
| 18 | A | C |
| 19 | A | C |
| 20 | A | A |
| 21 | B | C |
| 22 | A | C |
| 23 | A | C |
| 24 | A | C |
| 32 | B | A |
| 33 | A | B |
| 34 | B | B |
| 35 | B | B |
| 36 | A | B |
| 37 | A | C |
| 38 | A | B |

Example 40

Synthesis of 2-amino-6-(3,4-dimethoxyphenyl)-pyrido(3,2-d)pyrimidin-4(3H)-thione A suspension of 2-amino-6-(3,4-dimethoxyphenyl)-pyrido(3,2-d)pyrimidin-4(3H)-one (example 21 of WO 2006/069805) is treated according to the procedure of example 1 and converted into the title compound with a similar yield.

Example 41

Synthesis of 2-amino-4-methylthio-6-(3,4-dimethoxyphenyl)-pyrido(3,2-d) pyrimidine A solution of the 2-amino-6-(3,4-dimethoxyphenyl)-pyrido(3,2-d)pyrimidin-4(3H)-thione from example 40 is treated according to the procedure of example 2 and converted into the title compound with a similar yield.

Examples 42 to 53

Synthesis of 2-amino-4-substituted-6-(3,4-dimethoxyphenyl)-pyrido (3,2-d)pyrimidines A solution of the 2-amino-4-thiomethyl-6-(3,4-dimethoxyphenyl)-pyrido(3,2-d)pyrimidine of example 41 is treated according to the procedure of examples 3-14 and converted into the following compounds with similar yields:
2-amino-4-(2-propoxyethoxy)-6-(3,4-dimethoxyphenyl)pyrido(3,2-d)pyrimidine,
2-amino-4-(2-butoxyethoxy)-6-(3,4-dimethoxyphenyl)pyrido(3,2-d)pyrimidine,
2-amino-4-(1-ethoxy-2-propoxy)-6-(3,4-dimethoxyphenyl)pyrido(3,2-d)pyrimidine,
2-amino-4-(2-isopropoxyethoxy)-6-(3,4-dimethoxyphenyl)pyrido(3,2-d)pyrimidine,
2-amino-4-(2,2-difluoroethoxy)-6-(3,4-dimethoxyphenyl)pyrido(3,2-d)pyrimidine,
2-amino-4-[2-(methylthio)ethoxy]-6-(3,4-dimethoxyphenyl)pyrido(3,2-d)pyrimidine,
2-amino-4-(cyclobutoxy)-6-(3,4-dimethoxyphenyl)pyrido(3,2-d)pyrimidine,
2-amino-4-(cyclopentylmethoxy)-6-(3,4-dimethoxyphenyl)pyrido(3,2-d)pyrimidine,
2-amino-4-(cyclopentoxy)-6-(3,4-dimethoxyphenyl)pyrido(3,2-d)pyrimidine,
2-amino-4-(3-methyl-3-methoxybutoxy)-6-(3,4-dimethoxyphenyl)pyrido(3,2-d)pyrimidine,
2-amino-4-(2-methyl-3-buten-2-oxy)-6-(3,4-dimethoxyphenyl)pyrido(3,2-d)pyrimidine, and
2-amino-4-(3-pentyn-1-oxy)-6-(3,4-dimethoxyphenyl)pyrido(3,2-d)pyrimidine.

Example 54

Synthesis of 2-amino-4-(1,2,4-triazolyl)-6-(3,4-dimethoxyphenyl)-pyrido (3,2-d)pyrimidine A suspension of 2-amino-6-(3,4-dimethoxyphenyl)-pyrido(3,2-d)pyrimidin-4(3H)-one (example 21 of WO 2006/069805) is treated according to the procedure of example 15 and converted into the title compound with a similar yield.

Examples 55 to 58

Synthesis of 2-amino-4-substituted-6-(3,4-dimethoxyphenyl)-pyrido(3,2-d)pyrimidines A solution of the 2-amino-4-(1,2,4-triazolyl)-6-(3,4-dimethoxyphenyl)-pyrido(3,2-d) pyrimidine of example 54 is treated according to the procedure of examples 16-19 and converted into the following compounds with similar yields:
2-amino-4-[3(S)-tetrahydrofuranyloxy]-6-(4-fluorophenyl)-pyrido(3,2-d)pyrimidine,
2-amino-4-[3(R)-tetrahydrofuranyloxy]-6-(4-fluorophenyl)-pyrido(3,2-d)pyrimidine,
2-amino-4-[2-(methylsulfonyl)ethoxy]-6-(4-fluorophenyl)-pyrido(3,2-d)pyrimidine, and
2-amino-4-[hexahydrofuro(2,3-b)furan-3-oxy]-6-(4-fluorophenyl)-pyrido(3,2-d) pyrimidine.

Examples 59 to 65

Synthesis of 2-amino-4-substituted-6-(2-formylphenyl-pyrido(3,2-d) pyrimidines

A suspension of a 2-acetamido-4-substituted-6-chloro-pyrido[3,2-d]pyrimidine from one of examples 25 to 31 is treated with 2-formylphenylboronic acid according to the procedure of examples 32-38 and converted into the following compounds with similar yields:
2-amino-4-cyclohexyloxy-6-(2-formylphenyl)-pyrido(3,2-d)pyrimidine,
2-amino-4-(tetrahydro-2H-pyran-4-oxy)-6-(2-formylphenyl)-pyrido(3,2-d)pyrimidine,
2-amino-4-(tetrahydropyran-2-methoxy)-6-(2-formylphenyl)-pyrido(3,2-d)pyrimidine,
2-amino-4-(tetrahydro-2-furanylmethoxy)-6-(2-formylphenyl)-pyrido(3,2-d)pyrimidine,
2-amino-4-(tetrahydro-3-furanylmethoxy)-6-(2-formylphenyl)-pyrido(3,2-d)pyrimidine,
2-amino-4-[(S)-1-methoxy-2-propoxy]-6-(2-formylphenyl)-pyrido(3,2-d)pyrimidine, and
2-amino-4-[(R)-1-methoxy-2-propoxy]-6-(2-formylphenyl)-pyrido(3,2-d)pyrimidine.

Examples 66 to 72

Synthesis of 2-amino-4-substituted-6-(4-carboxyphenyl-Pyrido(3,2-d)pyrimidines

A suspension of a 2-acetamido-4-substituted-6-chloro-pyrido[3,2-d]pyrimidine from one of examples 25 to 31 is treated with 4-carboxyphenylboronic acid according to the procedure of examples 32-38 and converted into the following compounds with similar yields:
2-amino-4-cyclohexyloxy-6-(4-carboxyphenyl)-pyrido(3,2-d)pyrimidine,
2-amino-4-(tetrahydro-2H-pyran-4-oxy)-6-(4-carboxyphenyl)-pyrido(3,2-d)pyrimidine,
2-amino-4-(tetrahydropyran-2-methoxy)-6-(4-carboxyphenyl)-pyrido(3,2-d)pyrimidine,
2-amino-4-(tetrahydro-2-furanylmethoxy)-6-(4-carboxyphenyl)-pyrido(3,2-d)pyrimidine,
2-amino-4-(tetrahydro-3-furanylmethoxy)-6-(4-carboxyphenyl)-pyrido(3,2-d)pyrimidine,
2-amino-4-[(S)-1-methoxy-2-propoxy]-6-(4-carboxyphenyl)-pyrido(3,2-d)pyrimidine, and
2-amino-4-[(R)-1-methoxy-2-propoxy]-6-(4-carboxyphenyl)-pyrido(3,2-d)pyrimidine.

The invention claimed is:
1. A pyrido(3,2-d)pyrimidine derivative represented by the structural formula:

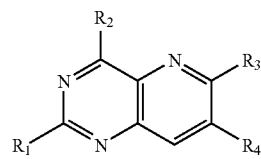

wherein:
R$_1$ is amino,
R$_2$ is selected from the group consisting of C$_{1-6}$ alkyl thio-C$_{1-6}$ alkoxy, C$_{2-6}$ alkenyloxy, C$_{2-6}$ alkynyloxy, C$_{3-10}$ cycloalkenyloxy, C$_{3-10}$ cycloalkenyl-C$_{1-6}$ alkoxy, C$_{1-6}$ alkylsulfonyl C$_{1-6}$ alkoxy, arylsulfonyl C$_{1-6}$ alkoxy, 2-propoxyethoxy, 2-ethoxy-1-propoxy, 2-isopropoxyethoxy, 2,2-difluoroethoxy, cyclobutoxy, cyclopentylmethoxy, 1-cyclopropylethoxy, 2-cyclopropylethoxy, cyclopentoxy, 3-methyl-3-methoxybutoxy, tetrahydrofuranyl-oxy, 1-ethylpropoxy, morpholinyl-propoxy, morpholinylbutoxy, cyclohexyloxy, tetrahydro-pyranoxy, tetrahydropyranmethoxy, tetrahydrofuranmethoxy, 1-methoxy-2-propoxy and oxetan-3-yloxy;

$R_3$ is selected from the group consisting of halogen, heterocyclic and aryl groups, wherein said heterocyclic or aryl groups are optionally substituted with one or more substituents selected from the group consisting of amino, amino-$C_{4-4}$ alkyl, acyl, di-$C_{1-4}$ alkylaminocarbonyl, $C_{1-4}$ alkoxy, $C_{1-4}$ alkylthio, $C_{1-4}$ alkyl, carboxylic acid, hydroxy, halogen, halo-$C_{1-4}$ alkyl, hydroxy-$C_{1-4}$ alkyl, halo-$C_{1-4}$ alkoxy, $C_{2-8}$ alkenyl, $C_{1-2}$ alkylenedioxy, $C_{1-4}$ alkylsulfonyl, $C_{1-4}$ alkoxycarbonyl, $C_{1-4}$ alkylcarbonyl-amino di-$C_{1-4}$ alkylamino, di-$C_{1-4}$ alkylamino-$C_{1-4}$ alkyl, aryl, aryl-$C_{1-4}$ alkoxy, aryloxy, formyl, heterocyclic, heterocyclic-oxy, tri-$C_{1-4}$ alkylammonium-$C_{1-4}$alkyl, $C_{1-4}$ alkylcarbonyl, $C_{1-4}$ alkylcarbonylamino, arylsulfonyl and heterocyclic-substituted $C_{1-4}$ alkyl, and $R_4$ is hydrogen, or a pharmaceutical acceptable addition salt or a stereochemical isomeric form thereof or a N-oxide thereof.

2. A pyrido(3,2-d)pyrimidine derivative according to claim 1, wherein $R_3$ is a mono-substituted phenyl group, wherein the substituent of said phenyl group is located in para position with respect to the pyrido(3,2-d)pyrimidinyl core.

3. A pyrido(3,2-d)pyrimidine derivative according to claim 1, wherein $R_3$ is a di-substituted phenyl group, wherein one substituent of said phenyl group is located in para position with respect to the pyrido(3,2-d)pyrimidinyl core.

4. A pyrido(3,2-d)pyrimidine derivative according to claim 1, wherein $R_3$ is a tri-substituted phenyl group.

5. A pyrido(3,2-d)pyrimidine derivative according to claim 1, wherein $R_3$ is a tri-substituted phenyl group wherein at least two substituents are identical.

6. A pyrido(3,2-d)pyrimidine derivative according to claim 1, wherein $R_3$ is a mono-substituted phenyl group and wherein the substituent of said phenyl group is located in meta position with respect to the pyrido(3,2-d)pyrimidinyl core.

7. A pyrido(3,2-d)pyrimidine derivative according to claim 1, wherein $R_3$ is a mono-substituted phenyl group and wherein the substituent of said phenyl group is located in ortho position with respect to the pyrido(3,2-d)pyrimidinyl core.

8. A pyrido(3,2-d)pyrimidine derivative according to claim 1, wherein $R_3$ is a di-substituted phenyl group, wherein one substituent of said phenyl group is located in ortho position with respect to the pyrido(3,2-d)pyrimidinyl core.

9. A pyrido(3,2-d)pyrimidine derivative according to claim 1, being selected from the group consisting of:

2-amino-4-(4-pentyn-1-oxy)-6-(4-fluorophenyl)pyrido(3,2-d)pyrimidine,
2-amino-4-(3-pentyn-1-oxy)-6-(4-fluorophenyl)pyrido(3,2-d)pyrimidine,
2-amino-4-(2-pentyn-1-oxy)-6-(4-fluorophenyl)pyrido(3,2-d)pyrimidine,
2-amino-4-(4-pentyn-2-oxy)-6-(4-fluorophenyl)pyrido(3,2-d)pyrimidine,
2-amino-4-(1-pentyn-3-oxy)-6-(4-fluorophenyl)pyrido(3,2-d)pyrimidine,
2-amino-4-[2-(methylsulfonyl)ethoxy]-6-(4-fluorophenyl)-pyrido(3,2-d) pyrimidine,
2-amino-4-[2-(phenylsulfonyl)ethoxy]-6-(4-fluorophenyl)-pyrido(3,2-d) pyrimidine,
2-amino-4-(3-butyn-1-oxy)-6-(4-fluorophenyl)pyrido(3,2-d)pyrimidine,
2-amino-4-(2-butyn-1-oxy)-6-(4-fluorophenyl)pyrido(3,2-d)pyrimidine,
2-amino-4-(2-propyn-1-oxy)-6-(4-fluorophenyl)pyrido(3,2-d)pyrimidine,
2-amino-4-(3-buten-1-oxy)-6-(4-fluorophenyl)pyrido(3,2-d)pyrimidine,
2-amino-4-(2-buten-1-oxy)-6-(4-fluorophenyl)pyrido(3,2-d)pyrimidine,
2-amino-4-(1-octen-3-oxy)-6-(4-fluorophenyl)pyrido(3,2-d)pyrimidine,
2-amino-4-(2-cyclohexen-1-oxy)-6-(4-fluorophenyl)pyrido(3,2-d)pyrimidine,
2-amino-4-(3-cyclohexen-1-methoxy)-6-(4-fluorophenyl)pyrido(3,2-d) pyrimidine, and
2-amino-4-(1,6-heptadien-4-oxy)-6-(4-fluorophenyl)pyrido(3,2-d) pyrimidine.

10. A pyrido(3,2-d)pyrimidine derivative selected from the group consisting of:

2-amino-6-(4-fluorophenyl)-pyrido(3,2-d)pyrimidin-4(3H)thione,
2-amino-4-methylthio-6-(4-fluorophenyl)-pyrido(3,2-d) pyrimidine,
2-amino-4-(2-propoxyethoxy)-6-(4-fluorophenyl)pyrido(3,2-d)pyrimidine,
2-amino-4-(2-butoxyethoxy)-6-(4-fluorophenyl)pyrido(3,2-d)pyrimidine,
2-amino-4-(1-ethoxy-2-propoxy)-6-(4-fluorophenyl)pyrido(3,2-d)pyrimidine,
2-amino-4-(2-isopropoxyethoxy)-6-(4-fluorophenyl)pyrido(3,2-d)pyrimidine,
2-amino-4-(2,2-difluoroethoxy)-6-(4-fluorophenyl)pyrido(3,2-d)pyrimidine,
2-amino-4-[2-(methylthio)ethoxy]-6-(4-fluorophenyl)pyrido(3,2-d)pyrimidine,
2-amino-4-(cyclobutoxy)-6-(4-fluorophenyl)pyrido(3,2-d)pyrimidine,
2-amino-4-(cyclopentylmethoxy)-6-(4-fluorophenyl)pyrido(3,2-d)pyrimidine,
2-amino-4-(cyclopentoxy)-6-(4-fluorophenyl)pyrido(3,2-d)pyrimidine,
2-amino-4-(3-methyl-3-methoxybutoxy)-6-(4-fluorophenyl)pyrido(3,2-d)pyrimi-dine,
2-amino-4-(2-methyl-3-buten-2-oxy)-6-(4-fluorophenyl)pyrido(3,2-d)pyrimidine,
2-amino-4-(3-pentyn-1-oxy)-6-(4-fluorophenyl)pyrido(3,2-d)pyrimidine,
2-amino-4-(1,2,4-triazolyl)-6-(4-fluorophenyl)-pyrido(3,2-d)pyrimidine,
2-amino-4-[3(S)-tetrahydrofuranyloxy]-6-(4-fluorophenyl)-pyrido(3,2-d)pyrimidine,
2-amino-4-[3(R)-tetrahydrofuranyloxy]-6-(4-fluorophenyl)-pyrido(3,2-d)pyrimidine,
2-amino-4-[2-(methylsulfonyl)ethoxy]-6-(4-fluorophenyl)-pyrido(3,2-d)pyrimidine,
2-amino-4-[hexahydro-furo(2,3-b)furan-3-oxy]-6-(4-fluorophenyl)-pyrido(3,2-d) pyrimidine,
2-acetamido-4-cyclohexyloxy-6-chloro-pyrido(3,2-d)pyrimidine,
2-acetamido-4-(tetrahydro-2H-pyran-4-oxy)-6-chloro-pyrido(3,2-d)pyrimidine,
2-acetamido-4-(tetrahydropyran-2-methoxy)-6-chloro-pyrido(3,2-d)pyrimidine,
2-acetamido-4-(tetrahydro-2-furanylmethoxy)-6-chloro-pyrido(3,2-d)pyrimidine,
2-acetamido-4-(tetrahydro-2-furanylmethoxy)-6-chloro-pyrido(3,2-d)pyrimidine,
2-acetamido-4-(tetrahydro-3-furanylmethoxy)-6-chloro-pyrido-(3,2-d) pyrimidine, 2-acetamido-4-[(S)-1-methoxy-2-propoxy]-6-chloro-pyrido(3,2-d)pyrimidine,
2-acetamido-4-[(R)-1-methoxy-2-propoxy]-6-chloro-pyrido(3,2-d)pyrimidine,
2-amino-4-cyclohexyloxy-6-(4-fluorophenyl)-pyrido(3,2-d)pyrimidine,
2-amino-4-(tetrahydro-2H-pyran-4-oxy)-6-(4-fluorophenyl)-pyrido(3,2-d)pyrimidine,
2-amino-4-(tetrahydropyran-2-methoxy)-6-(4-fluorophenyl)-pyrido(3,2-d)pyrimidine,
2-amino-4-(tetrahydro-2-furanylmethoxy)-6-(4-fluorophenyl)-pyrido(3,2-d)pyrimidine,
2-amino-4-(tetrahydro-3-furanylmethoxy)-6-(4-fluorophenyl)-pyrido(3,2-d)pyrimidine,
2-amino-4-(tetrahydro-3-tetrahydrofuranylmethoxy)-6-(4-fluorophenyl)-pyrido-(3,2-d) pyrimidine,
2-amino-4-[(S)-1-methoxy-2-propoxy]-6-(4-fluorophenyl)-pyrido(3,2-d)pyrimidine,
2-amino-4-[(R)-1-methoxy-2-propoxy]-6-(4-fluorophenyl)-pyrido(3,2-d)pyrimidine,
2-amino-6-(3,4-dimethoxyphenyl)-pyrido(3,2-d)pyrimidin-4(3H)-thione,
2-amino-4-methylthio-6-(3,4-dimethoxyphenyl)-pyrido(3,2-d) pyrimidine,
2-amino-4-(1-ethoxy-2-propoxy)-6-(3,4-dimethoxyphenyl)pyrido(3,2-d)pyrimidine,
2-amino-4-(2-isopropoxyethoxy)-6-(3,4-dimethoxyphenyl)pyrido(3,2-d)pyrimidine,
2-amino-4-(2,2-difluoroethoxy)-6-(3,4-dimethoxyphenyl)pyrido(3,2-d)pyrimidine,
2-amino-4-[2-(methylthio)ethoxy]-6-(3,4-dimethoxyphenyl)pyrido(3,2-d)pyrimidine,
2-amino-4-(cyclobutoxy)-6-(3,4-dimethoxyphenyl)pyrido(3,2-d)pyrimidine,
2-amino-4-(cyclopentylmethoxy)-6-(3,4-dimethoxyphenyl)pyrido(3,2-d)pyrimidine,
2-amino-4-(cyclopentoxy)-6-(3,4-dimethoxyphenyl)pyrido(3,2-d)pyrimidine,
2-amino-4-(3-methyl-3-methoxybutoxy)-6-(3,4-dimethoxyphenyl)pyrido(3,2-d)pyrimidine,
2-amino-4-(2-methyl-3-buten-2-oxy)-6-(3,4-dimethoxyphenyl)pyrido(3,2-d)pyrimidine,
2-amino-4-(3-pentyn-1-oxy)-6-(3,4-dimethoxyphenyl)pyrido(3,2-d)pyrimidine,
2-amino-4-[3(S)-tetrahydrofuranyloxy]-6-(4-fluorophenyl)-pyrido(3,2-d)pyrimidine,
2-amino-4-[3(R)-tetrahydrofuranyloxy]-6-(4-fluorophenyl)-pyrido(3,2-d)pyrimidine,
2-amino-4-[2-(methylsulfonyl)ethoxy]-6-(4-fluorophenyl)-pyrido(3,2-d)pyrimidine,
2-amino-4-[hexahydrofuro(2,3-b)furan-3-oxy]-6-(4-fluorophenyl)-pyrido(3,2-d) pyrimidine,
2-amino-4-cyclohexyloxy-6-(2-formylphenyl)-pyrido(3,2-d)pyrimidine,
2-amino-4-(tetrahydro-2H-pyran-4-oxy)-6-(2-formylphenyl)-pyrido(3,2-d)pyrimidine,
2-amino-4-(tetrahydropyran-2-methoxy)-6-(2-formylphenyl)-pyrido(3,2-d)pyrimidine,
2-amino-4-(tetrahydro-2-furanylmethoxy)-6-(2-formylphenyl)-pyrido(3,2-d)pyrimidine,
2-amino-4-(tetrahydro-3-furanylmethoxy)-6-(2-formylphenyl)-pyrido(3,2-d)pyrimidine,
2-amino-4-[(S)-1-methoxy-2-propoxy]-6-(2-formylphenyl)-pyrido(3,2-d)pyrimidine,
2-amino-4-[(R)-1-methoxy-2-propoxy]-6-(2-formylphenyl)-pyrido(3,2-d)pyrimidine,
2-amino-4-cyclohexyloxy-6-(4-carboxyphenyl)-pyrido(3,2-d)pyrimidine,
2-amino-4-(tetrahydro-2H-pyran-4-oxy)-6-(4-carboxyphenyl)-pyrido(3,2-d)pyrimidine,
2-amino-4-(tetrahydropyran-2-methoxy)-6-(4-carboxyphenyl)-pyrido(3,2-d)pyrimidine,
2-amino-4-(tetrahydro-2-furanylmethoxy)-6-(4-carboxyphenyl)-pyrido(3,2-d)pyrimidine,
2-amino-4-(tetrahydro-3-furanylmethoxy)-6-(4-carboxyphenyl)-pyrido(3,2-d)pyrimidine,
2-amino-4-[(S)-1-methoxy-2-propoxy]-6-(4-carboxyphenyl)-pyrido(3,2-d)pyrimidine, and
2-amino-4-[(R)-1-methoxy-2-propoxy]-6-(4-carboxyphenyl)-pyrido(3,2-d)pyrimidine.

11. A pharmaceutical composition comprising one or more pharmaceutically acceptable carriers and a pyrido(3,2-d)pyrimidine derivative according to claim 1.

12. A pharmaceutical composition according to claim 11, further comprising one or more antiviral agents.

13. A method of treatment of a patient suffering from a viral infection, comprising administering to said patient an effective amount of a pyrido(3,2-d)pyrimidine derivative according to claim 1.

14. A method of treatment according to claim 13, further comprising administering, simultaneously or sequentially, one or more other antiviral agents.

15. A method of treatment according to claim 13, wherein said viral infection is a HCV infection.

16. A method of treatment according to claim 14, wherein said viral infection is a HCV infection.

17. A pharmaceutical composition according to claim 12, further comprising one or more antiviral agents selected from the group consisting of interferons, ribavirin analogs, NS5b polymerase inhibitors, HCV NS3 protease inhibitors, alpha-glucosidase 1 inhibitors, hepatoprotectants, non-nucleoside inhibitors of HCV, and other drugs for treating HCV and mixtures thereof.

18. A method according to claim 16, further comprising administering, simultaneously or sequentially, one or more other antiviral agents selected from the group consisting of pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen+actimmune, IFN-omega with DUROS, albuferon, locteron, Albuferon, Rebif, Oral interferon alpha, IFNalpha-2b XL, AVI-005, PEG-Infergen, and Pegylated IFN-beta, rebetol, copegus, viramidine (taribavirin), NM-283, valopicitabine, R1626, PSI-6130 (R1656), HCV-796, BILB 1941, XTL-2125, MK-0608, NM-107, R7128 (R4048), VCH-759, PF-868554, GSK625433, SCH-503034 (SCH-7), VX-950 (telaprevir), BILN-2065, BMS-605339, ITMN-191, MX-3253 (celgosivir), UT-231B, IDN-6556, ME 3738, LB-84451, MitoQ, benzimidazole derivatives, benzo-1,2,4-thiadiazine derivatives, phenylalanine derivatives, GS-9190, A-831, A-689, zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

19. A pharmaceutical composition according to claim 12 further comprising one or more antiviral agents selected from the group consisting of ribavirin, (pegylated)interferon, HIV-1 IN inhibitors, zidovudine, lamivudine, didanosine, stavudine, nevirapine, delavirdine, foscarnet sodium, saquinavir, ritonavir, indinavir, nelfinavir, acemannan, acyclovir, adefovir, alovudine, alvircept, amantadine, aranotin, arildone, atevirdine, pyridine, cidofovir, cipamfylline, cytarabine, desciclovir, disoxaril, edoxudine, enviradene, enviroxime, famciclovir, famotine, fiacitabine, fialuridine, floxuridine, fosarilate, fosfonet, ganciclovir, idoxuridine, kethoxal, lobucavir, memotine, methisazone, penciclovir, pirodavir, somantadine, sorivudine, tilorone, trifluridine, valaciclovir, vidarabine, viroxime, zinviroxime, moroxydine, podophyllotoxin, ribavirine, rimantadine, stallimycine, statolon, tromantadine and xenazoic acid; and their pharmaceutically acceptable salts.

* * * * *